United States Patent
Errico et al.

(10) Patent No.: US 12,354,741 B2
(45) Date of Patent: *Jul. 8, 2025

(54) MEDICAL DEVICES FOR TREATING MEDICAL CONDITIONS

(71) Applicant: ElectroCore, Inc., Rockaway, NJ (US)

(72) Inventors: Joseph P. Errico, Palm Beach Gardens, FL (US); Francis R. Amato, Basking Ridge, NJ (US); Steven M. Mendez, Chester, NJ (US); Hecheng Hu, Cedar Knolls, NJ (US)

(73) Assignee: ELECTROCORE, INC., Rockaway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,545

(22) Filed: Nov. 15, 2023

(65) Prior Publication Data

US 2024/0087736 A1    Mar. 14, 2024

Related U.S. Application Data

(63) Continuation of application No. 18/099,159, filed on Jan. 19, 2023, now Pat. No. 11,854,695, which is a
(Continued)

(51) Int. Cl.
*G16H 40/63* (2018.01)
*G06K 7/14* (2006.01)
(Continued)

(52) U.S. Cl.
CPC ............ *G16H 40/63* (2018.01); *G06Q 20/20* (2013.01); *G06Q 20/202* (2013.01);
(Continued)

(58) Field of Classification Search
CPC ........ G16H 40/63; G16H 20/13; G16H 50/20; G06Q 20/20; G06Q 20/202; G06K 7/1413; G06K 7/1417
(Continued)

(56) References Cited

U.S. PATENT DOCUMENTS

2010/0179617 A1* 7/2010 Fletcher ............. A61N 1/37241
607/59
2011/0152967 A1* 6/2011 Simon .................... A61N 2/006
607/45
(Continued)

OTHER PUBLICATIONS

FDA, De Novo Classification Request for gammaCore Noninvasive Vagus Nerve Stimulator, Oct. 15, 2015, pp. 1-22, https://www.accessdata.fda.gov/cdrh_docs/reviews/DEN150048.pdf (Year: 2015).*

*Primary Examiner* — Joy Chng
(74) *Attorney, Agent, or Firm* — Farber LLC

(57) ABSTRACT

A medical device, such as a neurostimulator, is provided that includes a housing, a power supply, a signal generator and one or more electrodes coupled to the housing. The signal generator is configured to apply one or more electrical impulses to the one or more electrodes for a period of time, the period of time being defined as a single dose. The device is configured to switch from an activated mode and a deactivated mode after specific number of single doses have been emitted by the signal generator.

15 Claims, 26 Drawing Sheets

Related U.S. Application Data continuation of application No. 16/229,299, filed on Dec. 21, 2018, now Pat. No. 11,581,090.

(60) Provisional application No. 62/609,807, filed on Dec. 22, 2017.

(51) Int. Cl.
*G06Q 20/20* (2012.01)
*G16H 20/13* (2018.01)
*G16H 50/20* (2018.01)

(52) U.S. Cl.
CPC ............. *G16H 20/13* (2018.01); *G16H 50/20* (2018.01); *G06K 7/1413* (2013.01); *G06K 7/1417* (2013.01)

(58) Field of Classification Search
USPC ........................................................ 705/2–3
See application file for complete search history.

(56) References Cited

U.S. PATENT DOCUMENTS

| | | | | |
|---|---|---|---|---|
| 2014/0257438 A1* | 9/2014 | Simon | ...................... | A61N 2/02 607/150 |
| 2014/0324118 A1* | 10/2014 | Simon | .................. | A61B 5/4836 607/46 |
| 2015/0230760 A1* | 8/2015 | Schneider | ............. | A61M 5/172 600/300 |

\* cited by examiner

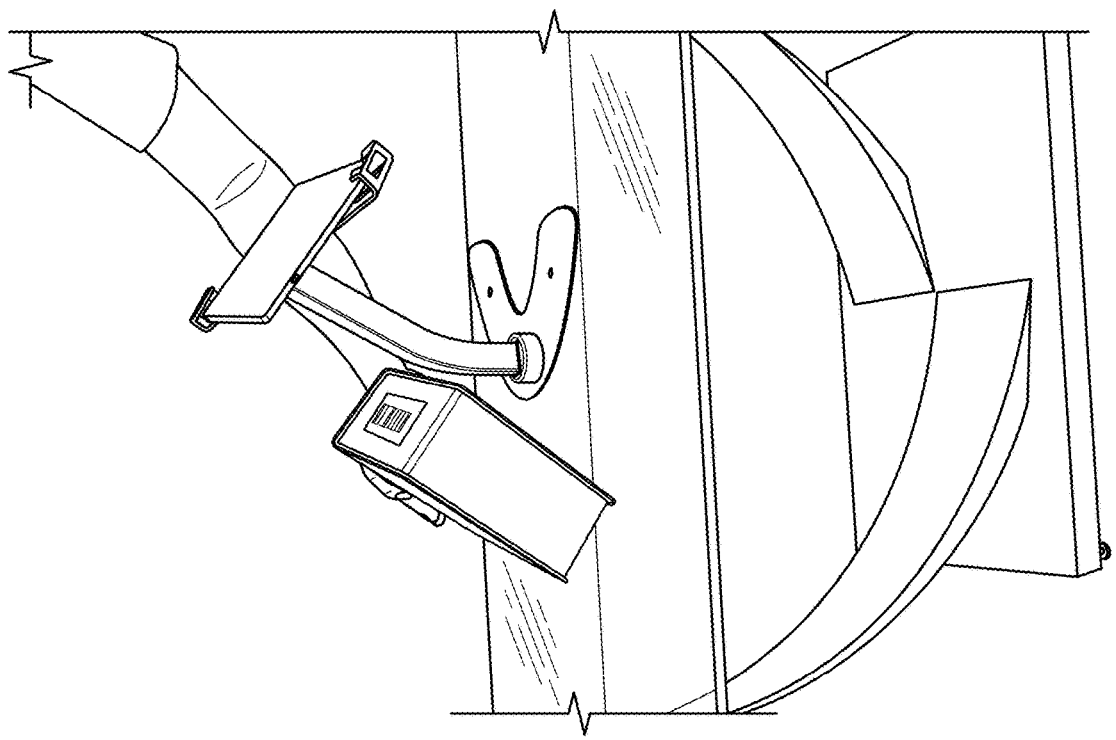
FIG. 8D
FIG. 8E

| | | | |
|---|---|---|---|
| Treatments Remaining | (24) | 86 (24) | 6 Treatments Remaining Within a 24 Hour Period |
| Stimulation Intensity | ⊞ | 23 ⊞ | Stimulation Intensity at 23, ⊞ Symbol Indicates a Signal at Stimulation Surfaces. Stimulation Intensity can Range from 1 - 40. |
| Days Remaining | 12 | 30 12 | 30 Days Remaining Until Device Expires and will not Deliver Treatments |
| Stimulation Intensity at Last Use | ☼ | 23 ☼ | Last Stimulation Intensity |
| Battery | ☼ | 90 ☼ | Battery Charge Indicator |
| Reload | @ | @ r | Refill Card is Being Read |

FIG. 9B

| | | | |
|---|---|---|---|
| Start Up / Ready for Use | Days Remaining Doses Remaining<br>30 ⟷ 06<br>2 Seconds | 1 Short Beep After Power ON | Follow "How to Use" Instructions |
| Device in Use | Stimulation Intensity (Min 1 - Max 40)<br>23 | Short Beep Each Time Intensity is Increased/ Decreased | Follow "How to Use" Instructions |
| Dose Complete | 1. Number of Days Remaining<br>30<br>2. Number of Days Remaining<br>06<br>3. Last Stimulation Level<br>23 | 2 Short Beeps | NONE: Device Turns Off Automatically |
| Error | E1 | Repeated Long Beeps | Device Turns Off Automatically After 10 Seconds<br><br>Restart Device (Turn Off and On Again)* |
| No Doses Remaining | 00 | Repeated Long Beeps | Device Turns Off Automatically<br><br>Maximum Number of Treatments Reached Within 24 Hours. Wait Until Next 24-hour Period |
| Expired/No Days Left | 00 | Repeated Long Beeps | Device Turns Off Automatically<br><br>Replace Device* |

FIG. 9C

| | | |
|---|---|---|
| Low Battery | [icon] | Repeated Long Beeps | Place in Charging Station |
| Dead Battery | None | None | Place in Charging Station |
| Charging | Battery Charge Indicator Bars Flash and Increases | None | Allow Device to Fully Charge |
| Charging Complete | [icon] | None | Remove Device from Charging Station, Device is Ready to Use |
| Device Not Aligned in Charging Station | [icon] | None | Ensure Device is Fully Seated in Charging Station |
| Charging Error | [icon] | Repeated Long Beeps | Remove Device From Charging Station and Place Back In*<br>Unplug Charging Base Power Adapter from the Outlet and Plug in Again* |
| Reloading Error | [icon] | None | Reset Device (Turn Off and On Again)* |
| Card Error | [icon] | None | Wait 24 Hours and Restart Device (Turn Off and On Again)* |

*If Error is not Resolved Contact Customer Service

MEDICAL DEVICES FOR TREATING MEDICAL CONDITIONS

CROSS-REFERENCE TO RELATED APPLICATIONS

This patent application is a continuation of U.S. Nonprovisional application Ser. No. 18/099,159, filed Jan. 19, 2023, which is a continuation of U.S. Nonprovisional application Ser. No. 16/229,299, filed Dec. 21, 2018, which claims the benefit of U.S. Provisional Application Ser. No. 62/609,807 filed 22 Dec. 2017; the complete disclosures of which are incorporated herein by reference for all purposes as if copied and pasted herein.

TECHNICAL FIELD

This description relates to medical devices.

BACKGROUND

There is a desire for a technology to enable an initial provisioning and a refilling of a medical device, such as a non-invasive neurostimulator. However, such technology does not exist. Therefore, this disclosure enables such technology.

SUMMARY

According to an embodiment of this disclosure, a system comprises: a processor; a memory coupled to the processor, wherein the memory stores a first content; a medical device coupled to the processor; and a reader coupled to the processor, wherein the reader is configured to read a second content from a storage medium other than the memory such that the processor switches the medical device from a first mode to a second mode based on the first content corresponding to the second content.

According to an embodiment of this disclosure, a method comprises: causing, via a processor, a memory to store a first content; causing, via the processor, a reader to read a second content from a storage medium other than the memory; and causing, via the processor, a medical device to switch from a first mode to a second mode based on the first content corresponding to the second content.

According to an embodiment of this disclosure, a method comprises: obtaining, via a point-of-sale (POS) terminal, a first content uniquely associated with a medical device; retrieving, via the POS terminal, a second content from a record of a database; writing, via the POS terminal, the first content into the record such that the first content is associated with the second content in the record; and taking an action with respect to the medical device responsive to the writing.

According to an embodiment of this disclosure, a method comprises: retrieving, via a point-of-sale (POS) terminal, a first content and a second content from a record of a database, wherein the first content is uniquely associated with a medical device; and programming, via the POS terminal, a storage medium based on the first content and the second content such that the medical device can be switched from a first mode to a second mode based on the storage medium being in proximity of the medical device.

According to an embodiment of this disclosure, a method comprises: causing, via a processor, a reader to read a content from a storage medium; causing, via the processor, a medical device to be switched from a first mode to a second mode; tracking, via the processor, a use of the medical device in the second mode; causing, via the processor, the medical device to be switched from the second mode to the first mode in response to a threshold being satisfied based on the use.

Note that this disclosure is embodied in various forms illustrated in a set of accompanying illustrative drawings and variations are contemplated as being a part of this disclosure, limited only by a scope of various claims recited below.

DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

FIGS. 8A-8G show an embodiment of a process of pairing a patient/card and a medical device thereby establishing a master patient/card to device mapping according to this disclosure.

FIGS. 9A-9J show an embodiment of a neurostimulator according to this disclosure.

DETAILED DESCRIPTION

Generally, this disclosure discloses a system that includes a medical device, such as a neurostimulator, and an input device, such as a reader, where the medical device is associated with a first content, such as in a one-to-one correspondence. The input device is configured to obtain a second content from a storage medium, such as a card, and then enable the medical device to be switched from a first mode, such as a deactivated mode, to a second mode, such as an activated mode, based on the first content corresponding to the second content, such as logically. Note though that this disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Figure 1A:
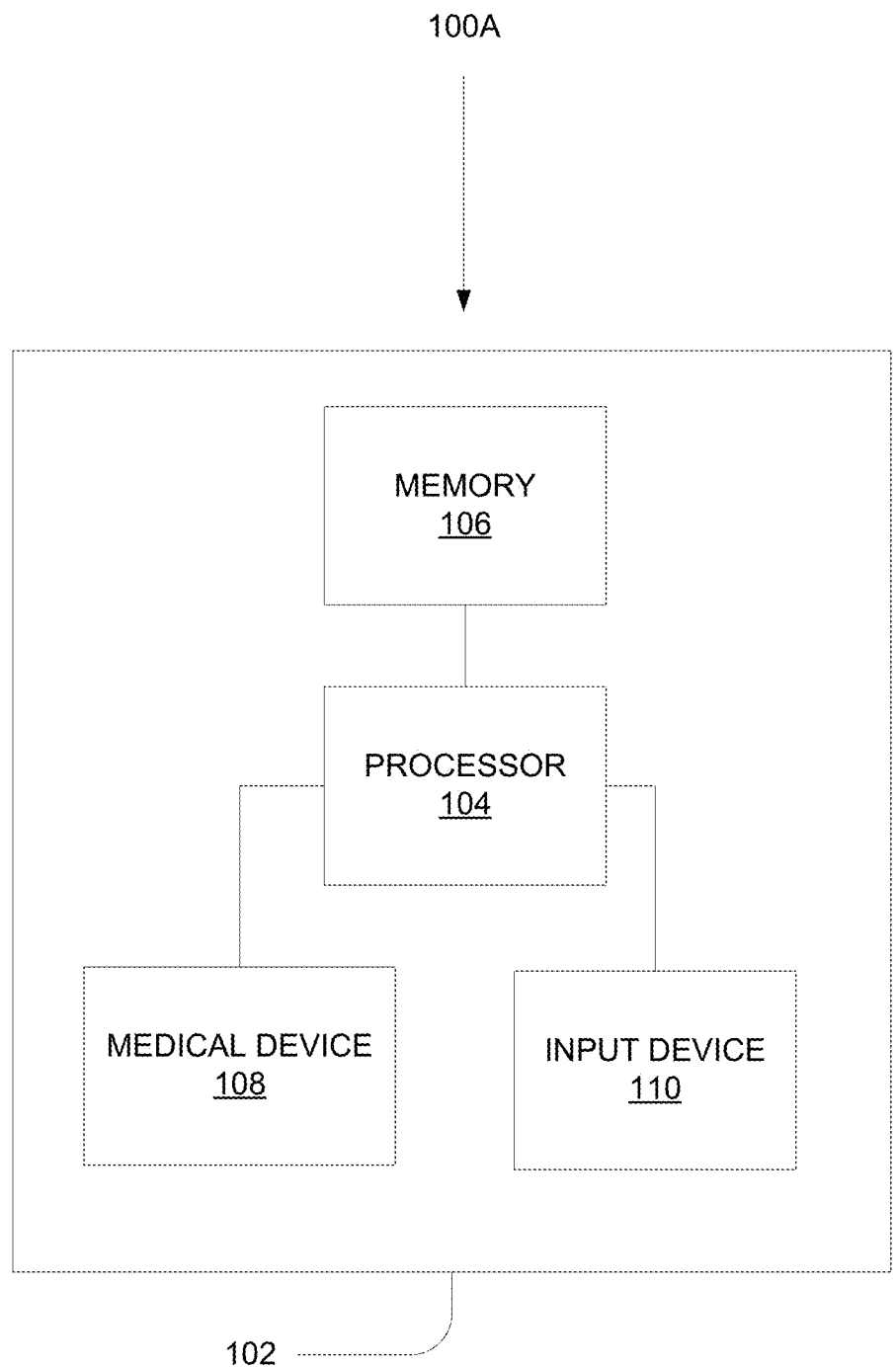
FIG. 1A shows a schematic diagram of an embodiment of a system containing a medical device and an input device according to this disclosure.
Figure 1B:
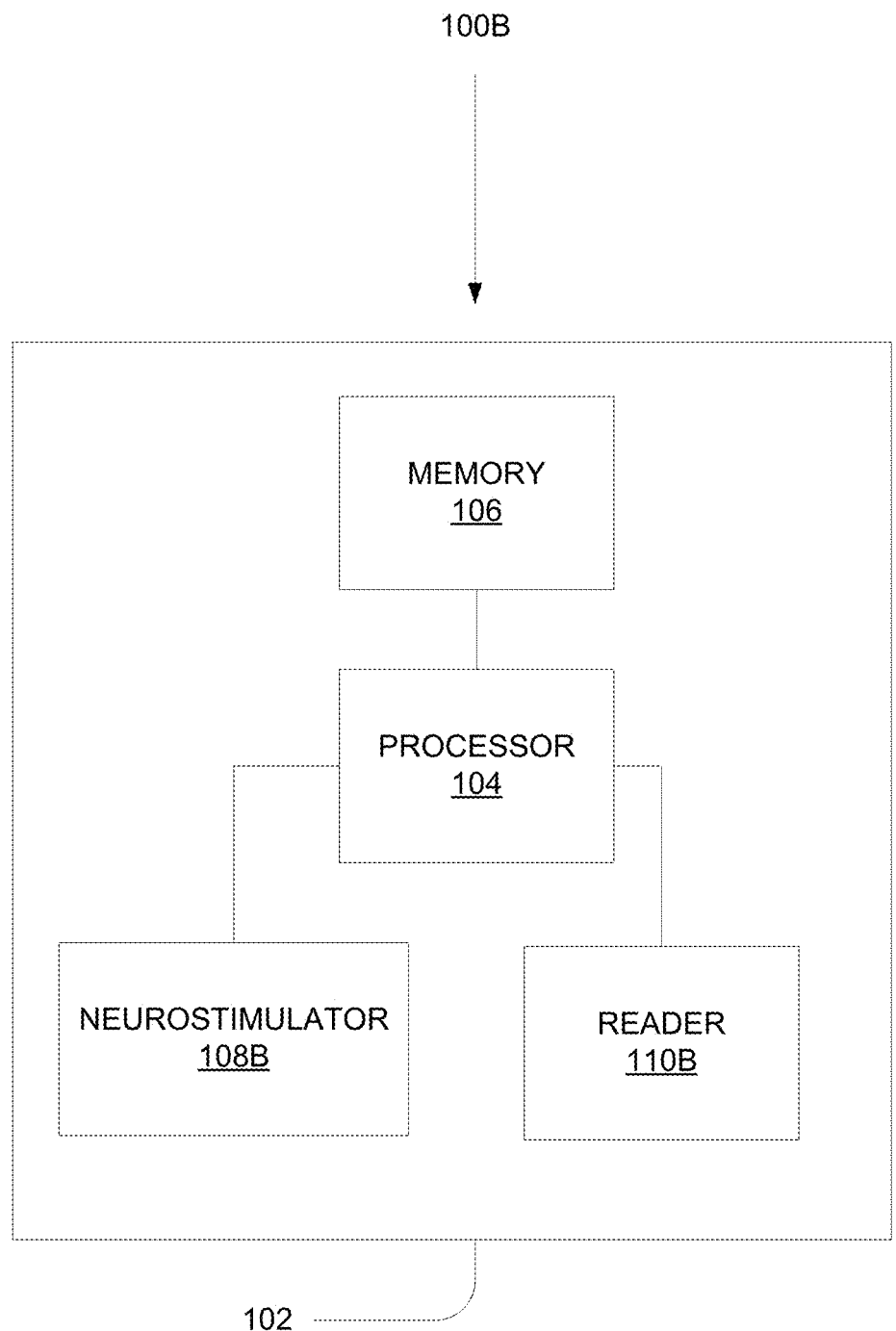
FIG. 1B shows a schematic diagram of an embodiment of a system containing a neurostimulator and a reader according to this disclosure.
Figure 1C:
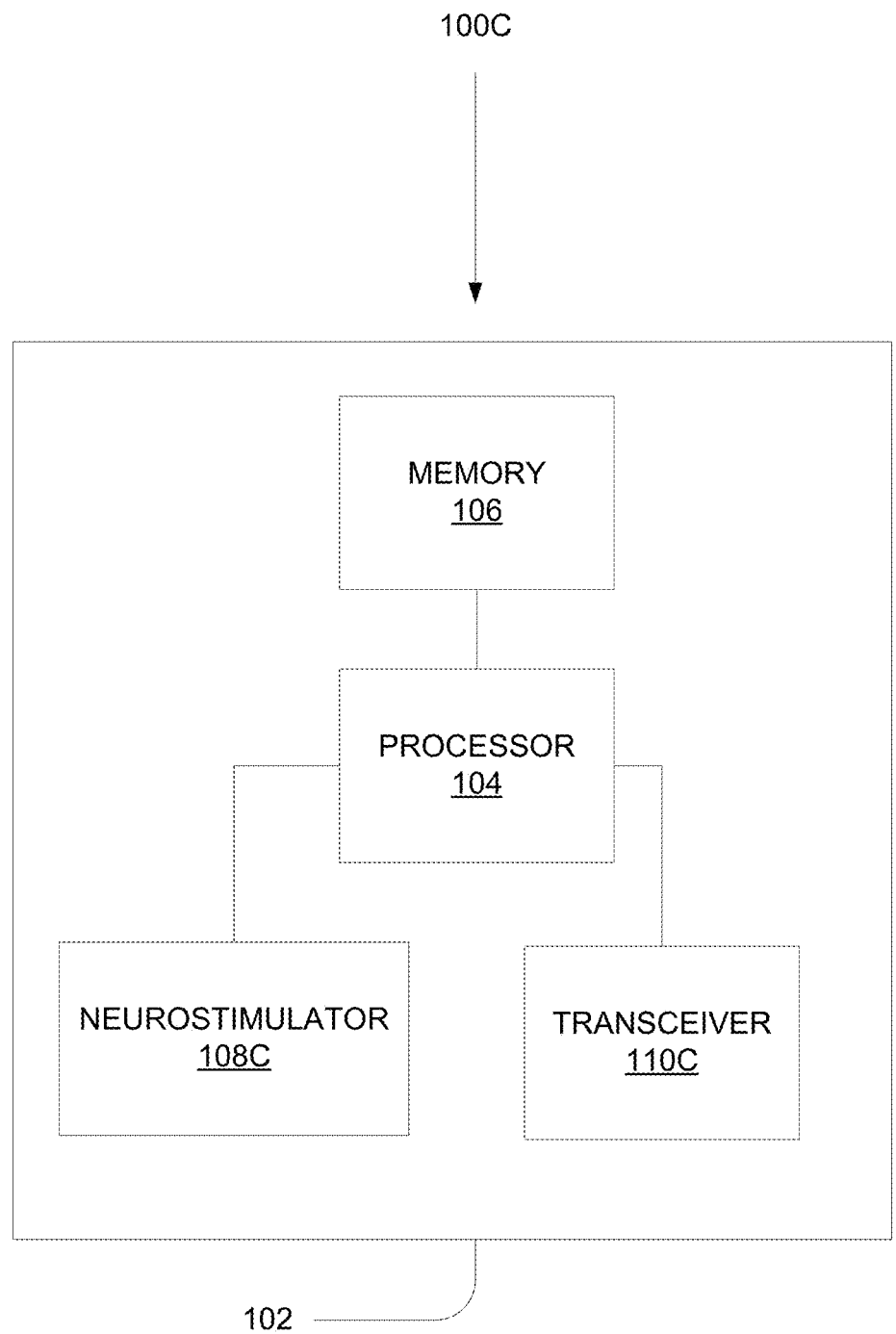
FIG. 1C shows a schematic diagram of an embodiment of a system containing a neurostimulator and a transceiver according to this disclosure.

FIG. 1A shows a schematic diagram of an embodiment of a system containing a medical device and an input device according to this disclosure. FIG. 1B shows a schematic diagram of an embodiment of a system containing a neurostimulator and a reader according to this disclosure. FIG. 1C shows a schematic diagram of an embodiment of a system containing a neurostimulator and a transceiver according to this disclosure. In particular, in FIG. 1A, a system 100A includes a housing 102, a processor 104, a memory 106, a medical device 108, and an input device 110. The system 100A is powered via a power source, such as a rechargeable or single-use battery, a mains powerline, a photovoltaic cell, a fluid turbine, or others. For example, when the system 100A is powered via the battery, then the battery can be positioned interior or exterior to the housing 102, yet securely supported via the housing 102 (e.g., fastening, mating, interlocking, adhering, hook-and-looping). For example, the battery can be rechargeable, whether over a wired, wireless, or waveguide connection, such as via a wireless charger housed or coupled to the housing 102. Similarly, when the system 100A is powered via the mains powerline, then the system 100A includes a conductive wire (e.g., copper, aluminum) or a cable (e.g., coaxial, data communication) spanning between the housing 102 and the mains powerline, with the conductive wire or the cable being coupled (e.g., mechanically, electrically) the housing 102, such as via a plug, a socket, a junction box, a pigtail, or others, and the mains powerline, such as via a plug, a socket, a junction box, a pigtail, or others.

The housing 102 houses (e.g., internally, externally) the processor 104, the memory 106, the medical device 108, and the input device 110. The housing 102 can include plastic, metal, rubber, or others. The housing 102 can be rigid, elastic, resilient, or flexible. For example, the housing 102 can be included in or embodied as a phone, a tablet, a laptop, a phone/tablet/laptop case, a patch, an adhesive bandage, a strip, an anklet, a belt, a bracelet, a necklace, a garment, a pad, a ring, a mattress, a pillow, a blanket, a robot, a surgical instrument, a stimulator, an infusion device, or others. For example, the housing 102 can be embodied as described in US Patent Application Publication 20140330336 and U.S. Pat. Nos. 8,874,205, 9,174,066, 9,205,258, 9,375,571, and 9,427,581, all of which are herein incorporated by reference for all purposes as if copied and pasted herein, such as all structures, all functions, and all methods of manufacture and use, as disclosed therein. As such, the medical device 108 can be embodied as described in US Patent Application Publication 20140330336 and U.S. Pat. Nos. 8,874,205, 9,174,066, 9,205,258, 9,375,571, and 9,427,581, all of which are herein incorporated by reference for all purposes as if copied and pasted herein, such as all structures, all functions, and all methods of manufacture and use, as disclosed therein.

In some embodiments, the housing 102 includes a plurality of housings 102, where the processor 104, the memory 106, the medical device 108, and the input device 110 are distributed (e.g., internally, externally) among the housings 102 in any permutational or combinatory manner. For example, one of the housings 102 may include the processor 104, the memory 106, whereas another of the housings 102 may include the medical device 108, and the input device 110, where the one of the housings 102 and the another of the housings 102 are signally coupled to each other, such as via wiring, wireless, transceivers, waveguides, or others. For example, one of the housings 102 may include the processor 104, the memory 106, and the medical device 108, whereas another of the housings 102 may include the input device 110, where the one of the housings 102 and the another of the housings 102 are signally coupled to each other, such as via wiring, wireless, transceivers, waveguides, or others.

In some embodiments, the housing 102 is anti-tamper, such as via a mechanic or chemical technique. Note that anti-tamper includes at least one of a tamper resistance, a tamper detection, a tamper response, or a tamper evidence. For example, the housing 102 can be mechanically anti-tamper via including a screw that can be operated with a non-standard bit. For example, the housing 102 can be chemically anti-tamper via including a tamper evident seal.

The processor 104 is coupled to the memory 106, the medical device 108, and the input device 110, such as via wiring, wireless, transceivers, waveguides, or others. The processor 104 can include a single core or multicore processor. The processor 104 can be included in or be a controller, such as a programmable logic controller (PLC) or others. The processor 104 can be distinct from the medical device 108 or be a component of the medical device 108.

The memory 106, whether volatile or non-volatile, is at least one of a mechanical memory, such as a punch card or others, or a semiconductor memory, such as a flash memory or others. The memory 106 can be distinct from the medical device 108 or be a component of the medical device 108. The memory 106 can receive, such as via a physical recordation, a wired or wireless connection, or others, and store a logic, such as projections, depressions, holes, modules, objects, programs, apps, firmware, microcode, or other forms of instruction, for execution via the processor 104. For example, the logic can be programmed or input via a (1) a manufacturer of the system 100A, (2) a distributor of the system 100A, (3) a retailer of the system 100A, (4) a wholesaler of the system 100A, or (5) a user of the system 100A, such as a medical service provider, a patient, or others. For example, a pharmacist can receive the system 100A programmed for use with a specific medical condition, disease, or disorder or a specific dosage or a specific patient or the pharmacist can receive the system 100A without being programmed for use with a specific medical condition, disease, or disorder or a specific dosage or a specific patient and then the pharmacist can program for use with a specific medical condition, disease, or disorder or a specific dosage or a specific patient, as disclosed herein. For example, a pharmacist or assistant thereof can program, such as over a wired or wireless connection, the logic via a pharmacy electronic terminal, which can include an electronic payment device, such as a payment card reader, a mobile phone wallet reader, a currency input device, a bill acceptor, a cash register, or others, or via a point-of-sale (POS) system, which may include some, most, or all of foregoing, and can be positioned in a customer interaction area or a back pharmacy or restricted personnel area, or others. Such programming can include input or modification of (1) patient identification information, such as personal information, biometrics (e.g., fingerprint, retina scan), or others, (2) medical condition, disease, or disorder type, (3) prevention, diagnosis, monitoring, amelioration, or treatment information, such as medical device operation parameters, such as dosages, timing, or others. For example, the logic can be executed via the processor 104, such as to authenticate users, to use or to track use of the medical device 108 for at least one of prevention, diagnosis, monitoring, amelioration, or treatment, to modify prescription data, to switch the medical device 108 between a plurality of modes, to communicate with other devices, accessories, peripherals, to reconfigure, retrofit, or update the medical device 108, or others.

The memory 106 also stores a first content, such as an activation code, a set of prescription data, a set of dosage/frequency of use data, or others, that is associated with the medical device 108, such as uniquely or others. For example, the first content can include a content (e.g., barcode, text, image, sound) that is unique with respect to other similar medical devices 108, such as a serial number, a device identifier, a device parameter, or others, or a plurality of medical devices listed in a database, as disclosed herein. The first content can be stored internal or external to the logic stored in the memory 106. The first content can be of any type, such as an alphanumeric, an image, a barcode, a sound, a data structure, a projection, a depression, a hole, or any others. The first content can be formatted in any manner, such as binary, denary, hexadecimal, or others.

The medical device 108 can include a sensor, such as one or more sensors, such as, for example, bio-sensors, feedback sensors, chemical sensors, optical sensors, acoustic sensors, vibration sensors, motion sensors, fluid sensors, radiation sensors, temperature sensors, motion sensors, proximity sensors, fluid sensors, or others. The sensor can be used to sense and detect various properties, conditions, and/or characteristics or variations to same or lack thereof. The sensor may generate an output, such as one or more outputs, which are communicated, via wire, wirelessly, or waveguide, to the medical device 108, a base station, processor, server, or other logic or computing device. The output may be used as an input to one or more of the foregoing devices to forecast or avert an imminent onset or predicted upcoming onset of a symptom, episode, condition or disease. For example, as disclosed in U.S. Patent App. Pub. No. 2017/0120052, which is incorporated herein by reference in its entirety for at least these purposes as if copied and pasted herein, as disclosed herein, and for all purposes as if copied and pasted herein, such as all structures, all functions, and all methods of manufacture and use, as disclosed therein.

The medical device 108 can be of any type to at least one of prevent, diagnose, monitor, ameliorate, or treat a medical condition, a disease, or a disorder of a patient, such as a mammal, such as an animal, such as a human, whether male or female, whether infant, child, adult, or elderly, or others.

For example, the medical device 108 can be configured to prevent, diagnose, monitor, ameliorate, or treat a neurological condition, such as epilepsy, headache/migraine, whether primary or secondary, whether cluster or tension, neuralgia, seizures, vertigo, dizziness, concussion, aneurysm, palsy, Parkinson's disease, Alzheimer's disease, or others, as understood to skilled artisans and which are only omitted here for brevity.

For example, the medical device 108 can be configured to prevent, diagnose, monitor, ameliorate, or treat neurological, neuropsychological, or neuropsychiatric activity, such as a modulation of neuronal function or processing to affect a functional outcome. The modulation of neuronal function can be useful with regard to diagnosing, monitoring, preventing, treating, or ameliorating neurological, psychiatric, psychological, conscious state, behavioral, mood, or thought activity. For example, this activity can manifests itself in a form of a disorder, such as attention or cognitive disorders (e.g., Autistic Spectrum Disorders), mood disorder (e.g., major depressive disorder, bipolar disorder, dysthymic disorder), anxiety disorder (e.g., panic disorder, posttraumatic stress disorder, obsessive-compulsive disorder, phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, enhancing or diminishing any neurological or psychiatric function not just an abnormality or disorder or others, as understood to skilled artisans and which are only omitted here for brevity. Neurological activity that may be modulated can include normal functions, such as alertness, conscious state, drive, fear, anger, anxiety, repetitive behavior, impulses, urges, obsessions, euphoria, sadness, and the fight or flight response, as well as instability, vertigo, dizziness, fatigue, photophobia, concentration dysfunction, memory disorders, headache, dizziness, irritability, fatigue, visual disturbances, sensitivity to noise (misophonia, hyperacusis, phonophobia), judgment problems, depression, symptoms of traumatic brain injury (whether physical, emotional, social, or chemical), autonomic functions, which includes sympathetic or parasympathetic functions (e.g., control of heart rate), somatic functions, or enteric functions.

For example, the medical device 108 can be configured to prevent, diagnose, monitor, ameliorate, or treat a neurodegenerative disease, such as Alzheimer's disease, Parkinson's disease, multiple sclerosis, postoperative cognitive dysfunction, and postoperative delirium, or others, as understood to skilled artisans and which are only omitted here for brevity.

For example, the medical device 108 can be configured to prevent, diagnose, monitor, ameliorate, or treat an inflammatory disorder, such as Alzheimer's disease, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, ulcerative colitis, chronic peptic ulcer, tuberculosis, periodontitis, sinusitis, hepatitis, or others, as understood to skilled artisans and which are only omitted here for brevity.

For example, the medical device 108 can be configured to prevent, diagnose, monitor, ameliorate, or treat a gastrointestinal condition, such as ileus, irritable bowel syndrome, Crohn's disease, ulcerative colitis, diverticulitis, gastroesophageal reflux disease, or others, as understood to skilled artisans and which are only omitted here for brevity.

For example, the medical device 108 can be configured to prevent, diagnose, monitor, ameliorate, or treat a bronchial disorder, such as asthma, bronchitis, pneumonia, or others, as understood to skilled artisans and which are only omitted here for brevity.

For example, the medical device 108 can be configured to prevent, diagnose, monitor, ameliorate, or treat a coronary artery disease, heart attack, arrhythmia, cardiomyopathy, or others, as understood to skilled artisans and which are only omitted here for brevity.

For example, the medical device 108 can be configured to prevent, diagnose, monitor, ameliorate, or treat a urinary disorder, such as urinary incontinence, urinalysis, overactive bladder, or others, as understood to skilled artisans and which are only omitted here for brevity.

For example, the medical device 108 can be configured to prevent, diagnose, monitor, ameliorate, or treat a cancer, such as bladder cancer, breast cancer, prostate cancer, lung cancer, colon or rectal cancer, skin cancer, thyroid cancer, brain cancer, leukemia, liver cancer, lymphoma, pancreatic cancer, or others, as understood to skilled artisans and which are only omitted here for brevity.

For example, the medical device 108 can be configured to prevent, diagnose, monitor, ameliorate, or treat a metabolic disorder, such as diabetes (type 1, type 2, or gestational), Gaucher's disease, sick cell anemia, cystic fibrosis, hemochromatosis, or others, as understood to skilled artisans and which are only omitted here for brevity.

The medical device 108 can be configured to output an energy via an energy source of the medical device 108, such as a mechanical energy via an actuation source (e.g., actuator) of the medical device 108, an electrical energy via a current or voltage source (e.g. electrode) of the medical device 108, an electromagnetic energy via an impulse source (e.g., generator) of the medical device 108, a thermal energy via a heating (e.g., heating element) or cooling (e.g., ice pack, fan) source of the medical device 108, an acoustic energy via an acoustic source (e.g., speaker, transducer) of the medical device 108, or a light energy via a light source (e.g., bulb, laser beam generator) of the medical device 108. For example, as shown in FIG. 1B, the medical device 108 can include a neurostimulator 108B, whether invasive, non-invasive, or hybrid. For example, the neurostimulator 108B can be embodied as described in US Patent Application Publication 2014/0330336 and U.S. Pat. Nos. 8,874,205, 9,037,247, 9,174,066, 9,205,258, 9,375,571, and 9,427,581, all of which are herein incorporated by reference for all purposes as if copied and pasted herein, such as all structures, all functions, and all methods of manufacture and use, as disclosed therein. For example, the neurostimulator can modulate central or peripheral nervous systems. For example, the neurostimulator can be enable spinal cord stimulation to provide therapy for intractable pain and refractory angina; occipital nerve stimulation to provide therapy for occipital neuralgia and transformed migraine; afferent vagus nerve modulation to provide therapy for a host of neurological and neuropsychiatric disorders, such as epilepsy, depression, Parkinson's disease, bulemia, anxiety/obsessive compulsive disorders, Alzheimer's disease, autism, and neurogenic pain; efferent vagus nerve stimulation for rate control in atrial fibrillation, and to provide therapy for congestive heart failure; gastric nerves or gastric wall stimulation to provide therapy for obesity; sacral nerve stimulation to provide therapy for urinary urge incontinence; deep brain stimulation to provide therapy for Parkinson's disease, and other neurological and neuropsychiatric disorders; cavernous nerve stimulation to provide therapy for erectile dysfunction. However, as explained herein, note that the medical device 108 can be of any type or modality for at least one of prevention, diagnosis, monitoring, amelioration, or treatment of a medical condition, disease, or a disorder of a patient. For example, the medical device 108 can be configured to output a fluid, such as a liquid, a suspension, or a gas. For example, the medical device 108 can be configured to output a gel, a powder, or a foam. For example, the medical device 108 can be configured to increase or decrease pressure or provide physical support, whether internal or external to a patient. An example of a device that can be used is a mechanical actuator, vibration device, piezoelectric device, electric motor (e.g., brushed, brushless) or engine (e.g., combustion) or any other force generator, applicator, or output device.

The medical device 108 can be configured to prevent, diagnose, monitor, ameliorate, or treat a medical condition, a disease, or a disorder of a patient based on a contact with or output of an energy (e.g., mechanical, electrical, thermal, acoustic, photonic) or a fluid (e.g., liquid, gas, gel, suspension, solution) or powder to various organ systems of human body or any components thereof. These organ systems can include a muscular system, such as human skeleton, joints, ligaments, or tendons. These organ systems can include a digestive system, such as mouth, salivary glands, pharynx, esophagus, stomach, small intestine, large intestine, liver, gallbladder, mesentery, pancreas, anal canal and anus, or appendix. These organ systems can include a respiratory system, such as nasal cavity, pharynx, larynx, trachea, bronchi, lungs, or diaphragm. These organ systems can include a urinary system, such as kidneys, ureters, bladder, or urethra. These organ systems can include a reproductive system, such as female reproductive system, ovaries, fallopian tubes, uterus, vagina, vulva, clitoris, placenta, male reproductive system, testes, epididymis, vas deferens, seminal vesicles, prostate, bulbourethral glands, penis, or scrotum. These organ systems can include an endocrine system, such as pituitary gland, pineal gland, thyroid gland, parathyroid glands, adrenal glands, or pancreas. These organ systems can include a circulatory system, such as heart, patent foramen ovale, arteries, veins, or capillaries. These organ systems can include a lymphatic system, such as lymphatic vessel, lymph node, bone marrow, thymus, spleen, or gut-associated lymphoid tissue. These organ systems can include a nervous system, such as brain, brainstem, cerebellum, spinal cord, ventricular system, peripheral nervous system, nerves, sensory organs, eye, ear, olfactory epithelium, or tongue. These organ systems can include integumentary system, such as mammary glands, skin, or subcutaneous tissue.

The medical device 108 can be configured to prevent, diagnose, monitor, ameliorate, or treat a medical condition, a disease, or a disorder of a patient based on a contact with or output of an energy (e.g., mechanical, electrical, thermal, acoustic, photonic) or a fluid (e.g., liquid, gas, gel, suspension, solution) or powder to various muscles of human body or any components thereof. These muscle systems include These muscle systems include forehead/eyelid, such as occipitofrontalis, occipitalis, frontalis, orbicularis oculi, corrugator supercilii, or depressor supercilii. These muscle systems include extraocular muscles, such as levator palpebrae superioris, superior tarsal, rectus muscles, or oblique muscles. These muscle systems include ear, such as auriculares, temporoparietalis, stapedius, or tensor tympani. These muscle systems include nose, such as procerus, nasalis, dilator naris, depressor septi nasi, or levator labii superioris alaeque nasi. These muscle systems include mouth, such as levator anguli oris, depressor anguli oris, levator labii superioris, depressor labii, inferioris, mentalis, buccinator, orbicularis oris, risorius, or zygomatic muscles. These muscle systems include mastication, such as masseter, temporalis, or pterygoid muscles. These muscle systems include tongue, such as genioglossus, hyoglossus, chondroglossus, styloglossus, or palatoglossus. These muscle systems include intrinsic, such as superior longitudinal, transversus, inferior longitudinal, or verticalis muscle. These muscle systems include soft palate, such as levator veli palatini, tensor veli palatini, musculus uvulae, palatoglossus, or palatopharyngeus. These muscle systems include pharynx, such as stylopharyngeus, salpingopharyngeus, or pharyngeal muscles. These muscle systems include larynx, such as cricothyroid, arytenoid, thyroarytenoid, or cricoarytenoid muscles. These muscle systems include clavicular, such as platysma, or sternocleidomastoid. These muscle systems include suprahyoid, such as digastric, stylohyoid, mylohyoid, or geniohyoid. These muscle systems include anterior, such as longus colli, longus capitis, rectus capitis anterior, or rectus capitis lateralis. These muscle systems include lateral, such as scalene muscles, levator scapulae, rectus capitis lateralis, obliquus capitis superior, or obliquus capitis inferior. These muscle systems include posterior, such as rectus capitis posterior minor, rectus capitis posterior major, semispinalis capitis, longissimus capitis, splenius capitis, obliquus capitis superior, or obliquus capitis inferior. These muscle systems include back, such as erector spinae, latissimus dorsi, transversospinales, interspinales, intertransversarii, or splenius muscles. These muscle systems include chest, such as intercostals, subcostales, transversus thoracis, levatores costarum, serratus posterior muscles, diaphragm. These muscle systems include abdomen, such as transversus abdominis, rectus abdominis, pyramidalis, cremaster, quadratus lumborum, or oblique muscles. These muscle systems include pelvis, such as coccygeus, or levator ani. These muscle systems include perineum, such as sphincter ani, superficial perineal pouch, or deep perineal pouch. These muscle systems include vertebral column, such as trapezius, latissimus dorsi, rhomboids, or levator scapulae. These muscle systems include thoracic walls, such as pectoralis major, pectoralis minor, subclavius, or serratus anterior. These muscle systems include shoulder, such as deltoid, teres major, rotator cuff, supraspinatus, infraspinatus, teres minor, or subscapularis. These muscle systems include arm anterior compartment, such as coracobrachialis, biceps brachii, or brachialis. These muscle systems include arm posterior compartment, such as triceps brachii, or anconeus. These muscle systems include forearm anterior compartment, such as pronator teres, flexor carpi radialis, palmaris longus, flexor carpi ulnaris, flexor digitorum superficialis, pronator quadratus, flexor digitorum profundus, or flexor pollicis longus. These muscle systems include forearm posterior compartment, such as extensor digitorum, extensor digiti minimi, extensor carpi ulnaris, mobile wad, supinator, extensor indicis, anatomical snuff box, or extensor pollicis brevis. These muscle systems include hand such as opponens pollicis, flexor pollicis brevis, abductor pollicis brevis, adductor pollicis, palmaris brevis, hypothenar, lumbrical, dorsal interossei, or palmar interossei. These muscle systems include lower limb, such as iliopsoas, tensor fasciae latae, gluteal muscles, lateral rotator group, superior gemellus, articularis genus, sartorius, quadriceps femoris, biceps femoris, semitendinosus, semimembranosus, or adductor muscles of the hip. These muscle systems include leg, such as tibialis anterior, extensor hallucis longus, extensor digitorum longus, fibularis tertius, triceps surae, popliteus, tarsal tunnel, longus, or brevis. These muscle systems include foot, such as extensor digitorum brevis, extensor hallucis brevis, abductor hallucis, flexor digitorum brevis, abductor digiti minimi, quadratus plantae, lumbrical muscle, flexor hallucis brevis, adductor hallucis, flexor digiti minimi brevis, dorsal interossei, or plantar interossei.

The medical device 108 can be configured to prevent, diagnose, monitor, ameliorate, or treat a medical condition, a disease, or a disorder of a patient based on a contact with or output of an energy (e.g., mechanical, electrical, thermal, acoustic, photonic) or a fluid (e.g., liquid, gas, gel, suspension, solution) or powder to various nerves of human body or any components thereof. These nerves include nerves, such as abdominal aortic plexus, abducens nerve, accessory nerve, accessory obturator nerve, alderman's nerve, anococcygeal nerve, ansa cervicalis, anterior interosseous nerve, anterior superior alveolar nerve, auerbach's plexus, auriculotemporal nerve, axillary nerve, brachial plexus, buccal branch of the facial nerve, buccal nerve, cardiac plexus, cavernous nerves, cavernous plexus, celiac ganglia, cervical branch of the facial nerve, cervical plexus, chorda tympani, ciliary ganglion, coccygeal nerve, cochlear nerve, common fibular nerve, common palmar digital nerves of median nerve, deep branch of the radial nerve, deep fibular nerve, deep petrosal nerve, deep temporal nerves, diagonal band of broca, digastric branch of facial nerve, dorsal branch of ulnar nerve, dorsal nerve of clitoris, dorsal nerve of the penis, dorsal scapular nerve, esophageal plexus, ethmoidal nerves, external laryngeal nerve, external nasal nerve, facial nerve, femoral nerve, frontal nerve, gastric plexuses, geniculate ganglion, genital branch of genitofemoral nerve, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerves, inferior cardiac nerve, inferior cervical ganglion, inferior gluteal nerve, inferior hypogastric plexus, inferior mesenteric plexus, inferior palpebral nerve, infraorbital nerve, infraorbital plexus, infratrochlear nerve, intercostal nerves, intercostobrachial nerve, intermediate cutaneous nerve, internal carotid plexus, internal laryngeal nerve, interneuron, jugular ganglion, lacrimal nerve, lateral cord, lateral cutaneous nerve of forearm, lateral cutaneous nerve of thigh, lateral pectoral nerve, lateral plantar nerve, lateral pterygoid nerve, lesser occipital nerve, lingual nerve, long ciliary nerves, long root of the ciliary ganglion, long thoracic nerve, lower subscapular nerve, lumbar nerves, lumbar plexus, lumbar splanchnic nerves, lumboinguinal nerve, lumbosacral plexus, lumbosacral trunk, mandibular nerve, marginal mandibular branch of facial nerve, masseteric nerve, maxillary nerve, medial cord, medial cutaneous nerve of arm, medial cutaneous nerve of forearm, medial cutaneous nerve, medial pectoral nerve, medial plantar nerve, medial pterygoid nerve, median nerve, meissner's plexus, mental nerve, middle cardiac nerve, middle cervical ganglion, middle meningeal nerve, motor nerve, muscular branches of the radial nerve, musculocutaneous nerve, mylohyoid nerve, nasociliary nerve, nasopalatine nerve, nerve of pterygoid canal, nerve to obturator internus, nerve to quadratus femoris, nerve to the piriformis, nerve to the stapedius, nerve to the subclavius, nervus intermedius, nervus spinosus, nodose ganglion, obturator nerve, oculomotor nerve, olfactory nerve, ophthalmic nerve, optic nerve, otic ganglion, ovarian plexus, palatine nerves, palmar branch of the median nerve, palmar branch of ulnar nerve, pancreatic plexus, patellar plexus, pelvic splanchnic nerves, perforating cutaneous nerve, perineal branches of posterior femoral cutaneous nerve, perineal nerve, petrous ganglion, pharyngeal branch of vagus nerve, pharyngeal branches of glossopharyngeal nerve, pharyngeal nerve, pharyngeal plexus, phrenic nerve, phrenic plexus, posterior auricular nerve, posterior branch of spinal nerve, posterior cord, posterior cutaneous nerve of arm, posterior cutaneous nerve of forearm, posterior cutaneous nerve of thigh, posterior scrotal nerves, posterior superior alveolar nerve, proper palmar digital nerves of median nerve, prostatic plexus (nervous), pterygopalatine ganglion, pudendal nerve, pudendal plexus, pulmonary branches of vagus nerve, radial nerve, recurrent laryngeal nerve, renal plexus, sacral plexus, sacral splanchnic nerves, saphenous nerve, sciatic nerve, semilunar ganglion, sensory nerve, short ciliary nerves, sphenopalatine nerves, splenic plexus, stylohyoid branch of facial nerve, subcostal nerve, submandibular ganglion, suboccipital nerve, superficial branch of the radial nerve, superficial fibular nerve, superior cardiac nerve, superior cervical ganglion, superior ganglion of glossopharyngeal nerve, superior ganglion of vagus nerve, superior gluteal nerve, superior hypogastric plexus, superior labial nerve, superior laryngeal nerve, superior lateral cutaneous nerve of arm, superior mesenteric plexus, superior rectal plexus, supraclavicular nerves, supraorbital nerve, suprarenal plexus, suprascapular nerve, supratrochlear nerve, sural nerve, sympathetic trunk, temporal branches of the facial nerve, third occipital nerve, thoracic aortic plexus, thoracic splanchnic nerves, thoracoabdominal nerves, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic branches of facial nerve, zygomatic nerve, zygomaticofacial nerve, or zygomaticotemporal nerve.

The medical device 108 can be configured to prevent, diagnose, monitor, ameliorate, or treat a medical condition, a disease, or a disorder of a patient based on a contact with or output of an energy (e.g., mechanical, electrical, thermal, acoustic, photonic) or a fluid (e.g., liquid, gas, gel, suspension, solution) or powder to various bones of human body or any components thereof. These bones include spine, such as cervical vertebrae, thoracic vertebrae, lumbar vertebrae, sacral vertebrae, or coccygeal vertebrae. These bones include chest, such as hyoid, sternum, or ribs. These bones include head, such as cranial bones, facial bones, hyoid bones, or middle ear. These bones include arm, such as humerus, pectoral girdle, hand, metacarpals, or phalanges of the hand. These bones include pelvis, such as hip bone, ilium, ischium, pubis, sacrum, or coccyx. These bones include leg, such as femur, patella, tibia, fibula, or foot.

The medical device 108 has at least a first mode and a second mode. As such, since the processor 104 is coupled (e.g., electrically, mechanically) to the medical device 108, the processor 104 is able to execute (e.g., serial, parallel) the logic stored on the memory 106 and thereby switch the medical device 108 between the first mode and the second mode based on an input, such as a trigger, a heuristic, an action, or others, and operate the medical device 108 in the first mode or the second mode based on a set of parameters, which may be accessible to or stored in or via the logic via the memory 106. For example, the first mode can be an off mode and the second mode can be an on mode or vice versa. Similarly, the first mode can be a deactivated mode and the second mode can be an activated mode or vice versa. However, note that (1) the medical device 108 can be in the on mode, yet still be in the deactivated mode, and (2) the medical device 108 can at least one of prevent, diagnose, monitor, ameliorate, or treat the medical condition, disease, or the disorder of the patient in the activated mode. However, note again that, within the activated mode, the medical device 108 may have a plurality of sub-modes as well, such as modes of prevention, diagnosis, monitoring, amelioration, or treatment of various types, intensities, dosages, or others, which can vary based on medical conditions, disorders, diseases, or conditions. For example, the medical device 108 can operate in a first manner during the first mode and in a second manner in the second mode, where the first manner is different from or identical to the second manner, such as in an amount of operation, in an intensity of operation, in a duration of operation, in a modality of operation, in an energy use of operation, or others. For example, when the processor 104 switches the medical device 108 from the first mode (e.g., a deactivated mode) to the second mode (e.g., an activate mode), then such switching can activate the medical device 108 for a specific time period or a number of diagnosis or treatment doses or other parameters or vice versa. For example, the amount of operation includes a number of individual doses of at least one of diagnosis or treatment doses, such as less than or more than 3 doses, 4 doses, 5 doses, 6 doses, 7 doses, 8 doses, 9 doses, 10 doses, 15 doses, 20 doses, 25 doses, 30 doses, 40 doses, 45 doses, 50 doses, 60 doses, 65 doses, 70 doses, 75 doses, 80 doses, 85 doses, 90 doses, 95 doses, 100 doses, 200 doses, 300 doses, 400 doses, 500 doses, 600 doses, 700 doses, 800 doses, 900 doses, 1000 doses, or any other amount of doses from 1 to 1000 or greater, or others, whether a dose is based on a single use or a set of uses within a predefined time period (e.g., milliseconds, seconds, minutes, hours, days, weeks, months, years). As such, the medical device 108 can be adjusted where the first mode and the second mode can be equal or unequal in amount of doses. Similarly, the intensity of operation includes a degree or type of intensity with which the medical device 108 at least one of prevents, diagnoses, monitors, ameliorates, or treats the medical condition, disease, or the disorder in the patient. For example, the first mode can be associated with a first prevention, diagnosis, monitoring, amelioration, or treatment signal/energy output and the second mode can be associated with a second prevention, diagnosis, monitoring, amelioration, or treatment signal/energy output, wherein the first signal/energy output is identical to or differs from the second signal/energy output in various parameters, such as a content, a format, an amplitude, a frequency, a time period, or others. As such, the medical device 108 can be adjusted to more intensely or less intensely prevent, diagnose, monitor, ameliorate, or treat based on switching between the first mode and the second mode. Likewise, the duration of operation includes a number of defined time periods during which the medical device can at least one of prevent, diagnose, monitor, ameliorate, or treat, such as a number of seconds, minutes, hours, days, weeks, months, or others, whether dependent on usage or independent of usage. As such, the medical device 108 can be adjusted to a least one of prevent, diagnose, monitor, ameliorate, or treat between a first defined time period and a second defined time period.

The input device 110 is configured to obtain, such as via reading, copying, or others, a second content from a storage medium, such as a magnetic card, a radio frequency identification (RFID) card, a chip card, a barcode, a Quick Response (QR) code, or others, such that the processor 104 switches the medical device 108 between the first mode and the second mode based on the first content corresponding to the second content, such as logically or others, or vice versa. The second content, such as an activation code, a set of prescription data, a set of dosage/frequency of use data, or others, can be associated with the medical device 108, such as uniquely or others, with a specific mode of operation, such as for preventing, diagnosing, monitoring, ameliorating, or treating a specific medical condition, disease, or disorder, or with a particular user, such as based on a user identifier, such as a personal identification number (PIN), a biometric, or others. Note that the particular user can be associated with the medical device 108, such as via a primary key of a relational database, as disclosed herein. For example, the primary key can be the PIN or another set of data such that the second content is unique to the particular user. In some embodiments, where the medical device 108 is shared among a plurality of users, the second content can be unique to one of the users, yet access control or authentication between the users can be controlled via another layer or form of identification, such as passwords, biometrics, or others, such as when the system 100A includes a user input device coupled to the processor 104. For example, the user input device can include a keyboard or dial, whether physical, virtual (e.g., display), or haptic (e.g., display), a biometric reader, a fob or tag, a barcode, or others.

The second content can be of any of type, whether identical to or different from the first content, such as an alphanumeric, an image, a barcode, a sound, a data structure, a projection, a depression, a hole, or any others. The second content can be formatted in any manner, whether identical to or different from the first content, such as binary, denary, hexadecimal, or others.

The input device 110 can be of any modality or type, such as a camera, a microphone, a sensor, a card reader, a signal receiver, or others. For example, as shown in FIG. 1B, the input device 110 includes a reader 110B, such as a reader terminal, that is configured to read the second content from the storage medium, such as a card, a display, an interface, a chip, a memory dongle, a paper, or others, whether the storage medium is in or out of a line-of-sight of the reader 110B. For example, when the storage medium is a card, which can include paper, cardboard, plastic, rubber, metal, wood, or others, and the reader 110B is a card reader, then the card can be embedded with at least one of a barcode, a magnetic strip, a computer chip, or another storage medium and the card reader can read the at least one of the barcode, the magnetic strip, the computer chip, or the another storage medium. For example, the memory dongle can include a Universal Serial Bus (USB) dongle, a CompactFlash (CF) card, Secure Digital (SD) card, a MultiMediaCard (MMC) card. Therefore, the card can be a dumb card, a smart card, a memory card, a Wiegand card, a proximity card, or others, whether contact or contactless. Correspondingly, the reader 110B can be a smart card reader, a memory card reader, a Wiegand card reader, a magnetic stripe reader, a proximity reader, or others, whether the reader 110B is a non-intelligent reader, a semi-intelligent reader, or an intelligent reader. The input device 110 can be distinct from the medical device 108 or be a component of the medical device 108. The memory 106 can include the storage medium (e.g., removable memory chip) or vice versa. The memory 106 can exclude the storage medium or vice versa.

Similarly, as shown in FIG. 1C, the input device 110 includes a transceiver 110C, which includes a receiver, that is configured to receive, whether over a wired, wireless, or waveguide connection, the second content from the storage medium, such a card, a phone, a tablet, a laptop, a wearable, or others, such via a radio technique, an optical technique, an acoustic technique, or others, whether the storage medium is in or out of a line-of-sight of the transceiver 110C. For example, the radio technique can include a RFID interrogation, a Wi-Fi communication, a Bluetooth communication, or other radio communication formats, which can be encrypted or unencrypted. For example, the optical technique can include a laser beam, an infrared beam, a Li-Fi connection, or others. Note that the transceiver can include a transmitter or a receiver.

The input device 110 can obtain the second content from the storage medium in various ways. For example, the input device 110 can obtain the second content electronically, optically, electromagnetically, mechanically, or others, whether the storage medium is in or out of a line-of-sight of the input device 110. For example, when the input device 110 is the reader 110B, as per FIG. 1B, then the input device 110 can read the second content from the storage medium based on at least one of a barcode of the storage medium (optically), a QR code of the storage medium (optically), a magnetic material of the storage medium (electromagnetically), a chip of the storage medium (electromagnetically), an integrated circuit of the storage medium (electronically), a non-volatile memory of the storage medium (electronically), a punched hole of the storage medium (mechanically), a tactile surface of the storage medium (mechanically), or others. Likewise, when the input device 110 is the transceiver 110C, then the input device 110 can read the second content from the storage medium via an RFID technique, such as via interrogation, whether the storage medium is passive or active. Note that in some embodiments, the input device 110 includes the reader 110B and the transceiver 110C.

The first content can correspond to the second content in various ways, such as logically, such as via a Boolean logic, or others. For example, the first content can match the second content in content, format, logic, parameters, encryption, or others. For example, the first content can be equal to the second content, whether in format or value. Similarly, the first content can be unequal to the second content, whether in format or value. Likewise, the first content can logically map to the second content, such as via a logical symmetry where the first content is same as the second content or where the first content is different from the second, but related in a relatively quick computational way. For example, such correspondence can be determined based on or via hashing the first content or the second content. In some embodiments, processor 104 or the input device 110 can convert the first content or the second content before determining whether the first content corresponds to the second content. For example, such conversion can involve a format or a content of the first content or the second content.

When the first content does not correspond to the second content, such as the first content does not match the second content in value and format or others, as described above, then the medical device 108 is not switched from the first mode, such as a deactivated mode, to the second mode, such as an activated mode. In some embodiments, when the first content does not correspond to the second content, then the medical device 108 is switched from the first mode to the second mode, but the second mode is as or less operational than the first mode. For example, the second mode is a default mode of operation, a minimal mode of operation, a demo mode of operation, a disabled mode of operation, a kiosk mode of operation, or others.

In some embodiments, the system 100 includes an output device, such as a signal transmitter, a light, sound, or vibration source, an actuator, a data writer, or others, coupled to the processor 104, whether over a wired, wireless, or waveguide connection, where the processor 104 is configured to instruct the output device to interface with the storage medium in response to the input device 110 reading the second content. For example, the output device can include a transmitter and the processor 104 can instruct the transmitter to send a signal to the storage medium such that the storage medium can receive and process the signal, which may involve acting based on such processing. For example, such action can allow deactivating the storage medium based on or after the medical device 108 is switched from the first mode, such as a deactivated mode, to the second mode, such as an activated mode. For example, the processor 104 can request the output device to interface with the storage medium such that the storage medium is locked from further reading, when the storage medium is enabled for such locking. Similarly, the processor 104 can request the output device to interface with the storage medium such that the second content on the storage medium is rendered unusable, when the storage medium is enabled for such data modification rights. Likewise, the processor 104 can request the output device to interface with the storage medium such that the second content on the storage medium is erased from the storage medium, whether temporarily or permanently, when the storage medium is enabled for such data modification rights. Also, the processor 104 can request the output device to interface with the storage medium such that the storage medium is reformatted, when the storage medium is enabled for such data modification rights. Additionally, the processor 104 can request the output device to interface with the storage medium such that the storage medium is modified from a first state to a second state, when the storage medium is enabled for such state modification rights, and where the first state is before the input device 110 obtains the second content from the storage medium, and where the second state is after the input device 110 obtains the second content from the storage medium. Note that such interfacing can include electronically or physically modifying the storage medium or a content or data format thereon. Note that the first state and the second state can differ from each other in various ways (e.g., more or less functionality, more or less energy use, more or less data reading or modification or deletion or reformatting rights). As such, the output device can be useful to lock or wipe the storage medium once the input device 110 reads the second content from the storage medium.

When the system 100A is used to at least one of prevent, diagnose, monitor, ameliorate, or treat the medical condition, disease, or the disorder of the patient, the processor 104 tracks such use and can take an action when a predetermined threshold is satisfied or not satisfied, such as via the logic stored via the memory 106. For example, the logic tracks a use of the medical device 108 and when a number of uses, as programmed in advance, satisfies or does not satisfy the predetermined threshold, then the processor 104 can take an action, such as switch the medical device 108 between the first mode, such as an activated mode, and the second mode, such as a deactivated mode, or vice versa. Note that the logic has access to or can modify the predetermined threshold. Further, note that the predetermined threshold can be based on a number of single uses within a predefined time period (e.g., within a day, a week, a month, a year) or a number of single uses regardless of any time limit. For example, the action can include activating the medical device 108, deactivating the medical device 108, creating, modifying, or deleting a prevention, diagnosis, monitoring, amelioration, or treatment parameter of the medical device 108, as stored via the medical device 108 or the memory 106, creating, modifying, or deleting a set of treatment instructions of the medical device 108, as stored via the medical device 108 or the memory 106, or others.

In one mode of operation, a user of the system 100A positions the storage medium in proximity thereof, such as within about ten feet or less. The input device 110 interfaces with the storage medium such that the processor 104 switches the medical device 108 between the first mode and the second mode. If the first mode was a deactivated mode and the second mode was an activated mode, then the user can use the system 100A to prevent, diagnose, monitor, ameliorate, or treat the medical condition, disease, or the disorder of the user or another. For example, the input device 110 can read the second content from the storage medium and pass the second content to the processor 104. In response, the processor 104 can confirm that the first content, which is uniquely associated with the medical device 108, matches the second card, such as via value and format. Upon such confirmation, the processor 104 switches the medical device 108 from the first mode to the second mode.

Figure 2:
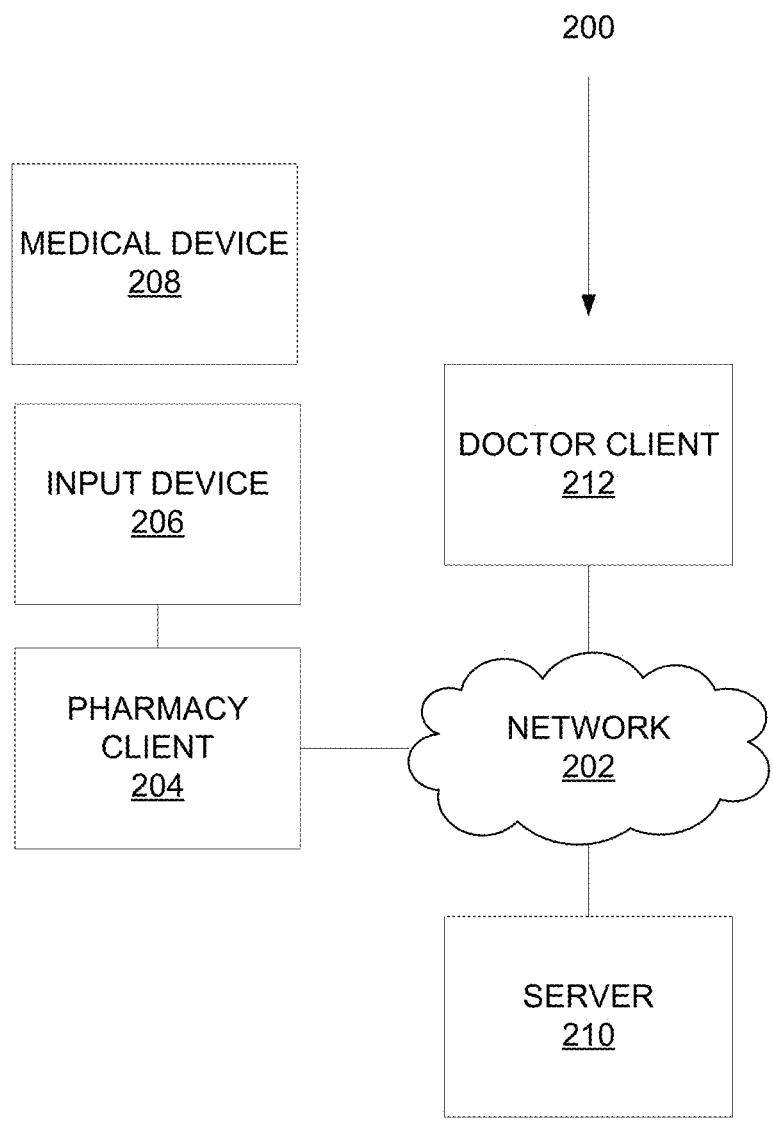
FIG. 2 shows a schematic diagram of an embodiment of a network diagram for initially provisioning and refilling a system containing a medical device according to this disclosure.
Figure 3:
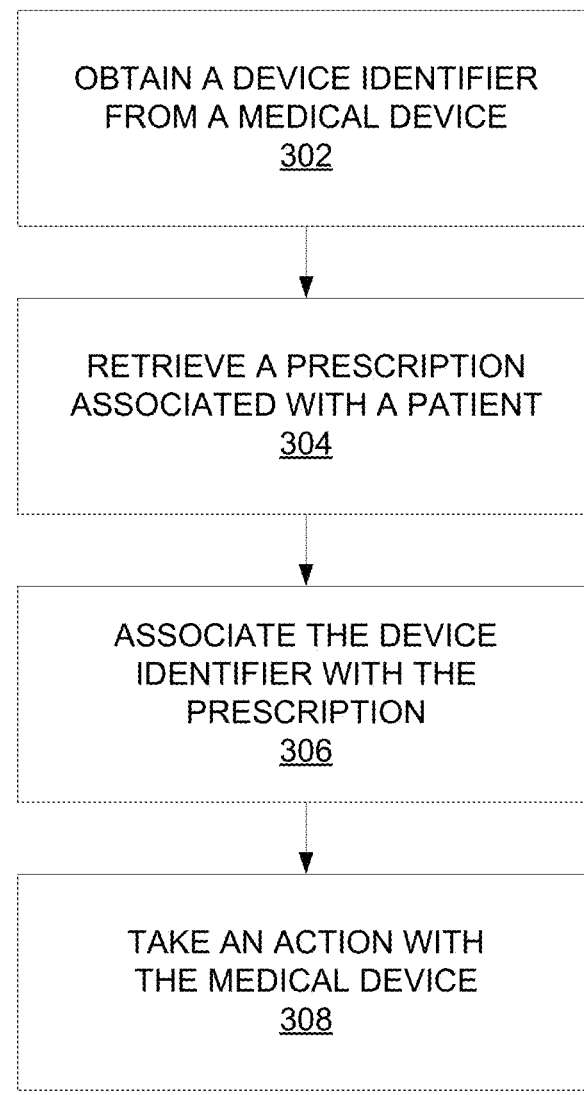
FIG. 3 shows a flowchart of an embodiment of a method for initially provisioning a system containing a medical device according to this disclosure.

FIG. 2 shows a schematic diagram of an embodiment of a network diagram for initially provisioning and refilling a system containing a medical device according to this disclosure. FIG. 3 shows a flowchart of an embodiment of a method for initially provisioning a system containing a medical device according to this disclosure. In particular, a system 200 includes a network 202, a pharmacy client 204, an input device 206, a medical device 208, a server 210, and a doctor client 212. The network 202 is in communication, whether over a wireless, wired, or waveguide connection, with the pharmacy client 204, the server 210, and the doctor client 212. The pharmacy client 204 is in communication, whether over a wireless, wired, or waveguide connection, with the input device 206 and the network 202.

The network 202 includes a plurality of nodes that allow for sharing of resources or information. The network 202 can be wired or wireless. For example, the network 202 can be a local area network (LAN), a wide area network (WAN), a cellular network, a satellite network, or others.

Each of the pharmacy client 204 and the doctor client 212 is a workstation that runs an operating system, such as MacOS®, Windows®, or others, and an application, such as an administrator application, on the operating system. The workstation can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, a barcode or QR code reader, or any other suitable input device. The workstation can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic. As such, the application presents a graphical user interface (GUI) configured to interact with a user to perform various functionality, as disclosed herein. In some embodiments, the application on the pharmacy client 204 can operate in an administrator mode and a kiosk mode, such as an agent mode or others, where the administrator mode has more or higher access privileges than the kiosk mode, where the kiosk mode is used for programming the medical device 208 or coupling the medical device 208 to the storage medium, as disclosed herein. Note that the application on the pharmacy client 204 can control access between the administrator mode and the kiosk mode via user identifiers, passwords, biometrics, or others. Further, note that at least one of the pharmacy client 204 or the doctor client 212 can be a non-workstation computer as well, such as a smartphone, a tablet, a laptop, a wearable, an eyewear unit, or others.

The server 210 runs an operating system, such as MacOS®, Windows®, or others, and an application, such as a prescription management application, on the operating system. In some embodiments, the server 210 hosts or has access to a database, such as a relational database, an in-memory database, a graphical database, a NoSQL database, or others. For example, the database can include a plurality of records, where each of the records contains a plurality of fields associated with a plurality of categories, such as patient identifier, patient contact information, patient medical record, prescription name, prescription dosage, and others. Note that the database can include or be coupled to an electronic medical records (EMR) database, whether local or remote thereto, whether using a same or different schema (e.g., star, tree). The server 210 can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, or any other suitable input device. The server 210 can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic.

The input device 206 is coupled to the pharmacy client 204, whether over in a wired, wireless, or waveguide connection, and can include a camera, a microphone, a keyboard, whether physical or virtual, a reader, or others. The input device 204 can be battery powered or powered via the pharmacy client 204.

The medical device 208, such as the system 100A, the medical device 108, or others, comprises a device identifier, such as the first content, as disclosed herein, whether internally, such as via the memory 106 or others, or externally, such as on the medical device 108 itself, on a tag coupled to the medical device 108, such as via adhering, fastening, mating, or others, or on a tag coupled to or depicted or printed on a package containing the medical device 208.

In one mode of operation, as shown in FIG. 3, in order to initially provision the medical device 208, the doctor client 212 sends a set of prescription data to the server 210 over the network 202. As per block 304, the pharmacy client 204 retrieves (e.g., reads, copies) the set of prescription data from the server 210 over the network 202, such as via a patient identifier associated with a record of the database accessible to the server 210. Upon retrieval, the pharmacy client 204 displays the set of prescription data thereon.

As per block 302, a user of the pharmacy client 204 uses the input device 206 to obtain the device identifier from the medical device 208. For example, when the device identifier, such as the first content, is internal to the medical device 208, then the input device 206 can interface with the medical device 208, whether over a wired, wireless, or waveguide connection, and obtain the device identifier, such as via an RFID interrogation or others. Likewise, when the device identifier is external to the medical device 208, then the input device 206 obtains the device identifier via reading the device identifier, such as via barcode or QR code scanning or others. Note that the block 302 can occur before, during, or after the block 304. As such, once the pharmacy client 204 has the device identifier and the set of prescription data, as per block 306, the pharmacy client 204 associates the device identifier and the set of prescription data, whether locally or on the server 210, such as via relating the device identifier and the set of prescription data in the database, such as via a primary key or others. Therefore, as per block 308, an action can be taken with the medical device 208. For example, the action can be via the pharmacy client 210 prompting a message that the medical device 208 is associated with the set of prescription data, generating a sound alert, modifying a data structure, or others. Similarly, the action can include packaging or repackaging the medical device 208, shipping the medical device 208, handing over the medical device 208 to a patient, or others.

Figure 4:
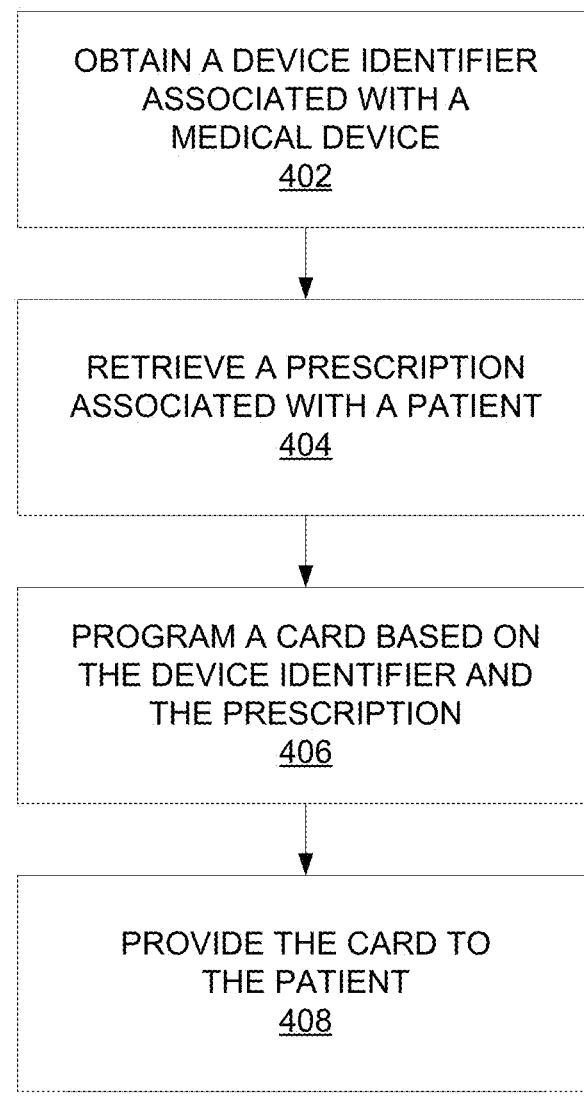
FIG. 4 shows a flowchart of an embodiment of a method for refilling a system containing a medical device according to this disclosure.

FIG. 4 shows a flowchart of an embodiment of a method for refilling a system containing a medical device according to this disclosure. In particular, in order to refill the medical device 208, the doctor client 212 sends a set of prescription data to the server 210 over the network 202. As per block 404, the pharmacy client 204 retrieves (e.g., reads, copies) the set of prescription data from the server 210 over the network 202, such as via a patient identifier associated with a record of the database accessible to the server 210. Upon retrieval, the pharmacy client 204 displays the set of prescription data thereon.

As per block 402, a user of the pharmacy client 204 uses the input device 206 to obtain the device identifier from the medical device 208. For example, when the device identifier, such as the first content, is internal to the medical device 208, then the input device 206 can interface with the medical device 208, whether over a wired, wireless, or waveguide connection, and obtain the device identifier, such as via an RFID interrogation or others. Likewise, when the device identifier is external to the medical device 208, then the input device 206 obtains the device identifier via reading the device identifier, such as via barcode or QR code scanning or others. Note that the block 402 can occur before, during, or after the block 404.

As such, once the pharmacy client 204 has the device identifier and the set of prescription data, as per block 406, the pharmacy client 204 can be used to program or reprogram a storage medium, such as an RFID card or others, based on the set of prescription data, via an output device, such as a signal transmitter, a light, sound, or vibration source, an actuator, a data writer, or others, coupled to the pharmacy client 204, whether over a wired, wireless, or waveguide connection. For example, such programming can be via an RFID interrogation or other technologies. For example, such programming can involve using the pharmacy client 204 to program the storage medium to match the device identifier that is uniquely associated with the medical device 208. For example, the pharmacy client 204 can instruct the output device to interface with the storage medium, such as via adding, modifying, or deleting content or format to or from the storage medium such that the storage medium stores the set of prescription data or a logic containing a set of instructions to operate the medical device 208 according to the set of prescription data. Note that this logic can be included in the set of prescription data or generated via the server 210 or the pharmacy client 204 based on the set of prescription data. In some embodiments, the medical device 208 generates this logic based on the set of prescription data as obtained from the storage medium. Therefore, the storage medium can be positioned in proximity (e.g., within about 10 feet or less) of the system 100A to be read via the input device 110 such that the processor 104 can switch the medical device 108 between the first mode and the second mode. Note that for recordkeeping purposes, the pharmacy client 204 can communicate (e.g., email, texting, social networking, over-the-top) a message informative of such programming to the server 210 over the network 202, such as for writing into the record of the patient in the database. For example, the pharmacy client 204 associates the device identifier and the set of prescription data, whether locally or on the server 210, such as via relating the device identifier and the set of prescription data in the database, such as via a primary key or others.

Consequently, as per block 408, the storage medium, as programmed, can be provided to the patient, such as via handing over to the patient, packaging/shipping to the patient, or communicating to the patient, such as via email, text, social networking, over-the-top messaging, or others. As such, a POS terminal, such as the pharmacy client 204, can be used to (1) obtain a device identifier from the medical device 208, (2) retrieve a set of prescription data from the server 210, where the device identifier is uniquely associated with the medical device 208, and (3) program, such as via encoding or others, a storage medium, such as an RFID card or others, based on the device identifier and the set of prescription data such that the medical device 208 can be switched from a first mode, such as a deactivated mode, to a second mode, such as an activated mode, or load a set of new therapy dose data, based on the storage medium being in proximity of the medical device 208.

In some embodiments, the output device can include a transmitter (e.g., wired, wireless, waveguide) and the pharmacy client 204 can instruct the transmitter to send (e.g., wired, wireless, waveguide) a signal to the storage medium such that the storage medium can receive and process the signal, which may involve acting based on such processing. For example, the pharmacy client 204 can request the output device to interface with the storage medium such that the storage medium is locked from further reading or writing or modifying or deleting, whether in data or format, when the storage medium is enabled for such locking. Similarly, the pharmacy client 204 can request the output device to interface with the storage medium such that the second content on the storage medium is rendered unusable, when the storage medium is enabled for such data modification rights. Likewise, the pharmacy client 204 can request the output device to interface with the storage medium such that the second content on the storage medium is erased from the storage medium, whether temporarily or permanently, when the storage medium is enabled for such data modification rights. Also, the pharmacy client 204 can request the output device to interface with the storage medium such that the storage medium is reformatted, when the storage medium is enabled for such data modification rights. Note that such interfacing can include electronically or physically modifying the storage medium or a content or a data format or an encryption thereon.

Figure 5:
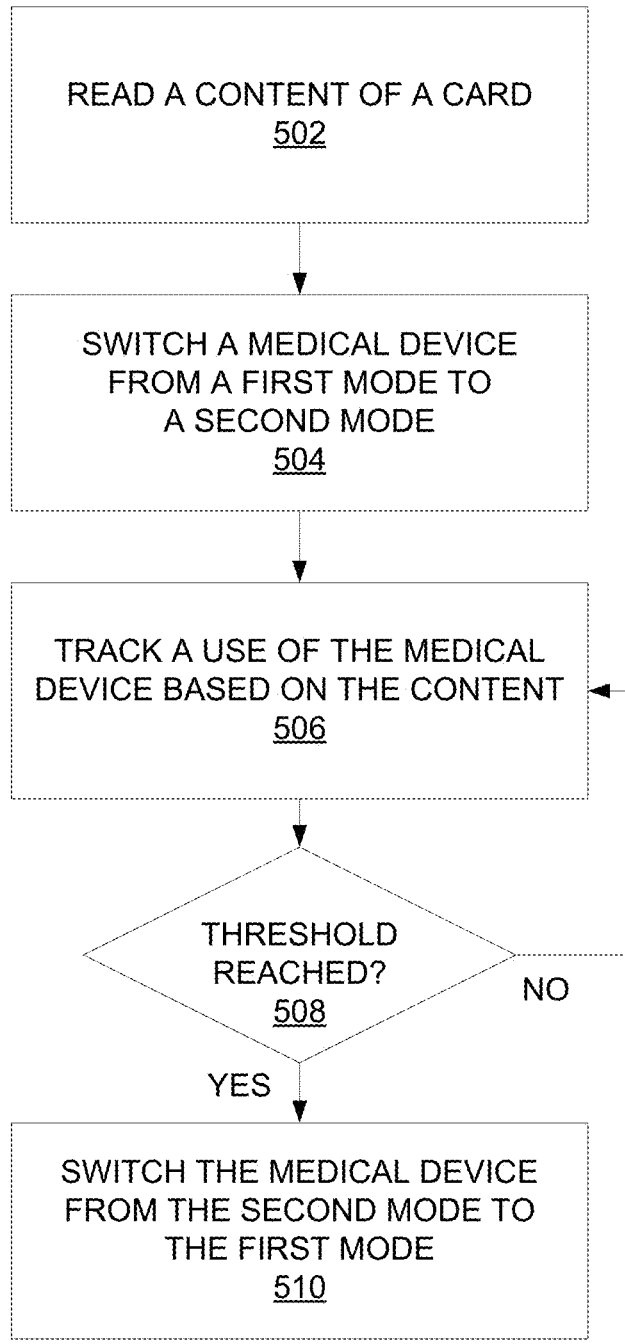
FIG. 5 shows a flowchart of an embodiment of a method for using a system containing a medical device according to this disclosure.

FIG. 5 shows a flowchart of an embodiment of a method for using a system containing a medical device according to this disclosure. In particular, as per block 502, a storage medium, such as an RFID card or others, is positioned in proximity of the input device 110, such as an RFID reader, such that the input device 110 can read a content of the storage medium. For example, the content can include an activation code and a set of prescription data, such as a therapy dosage or others. For example, such reading can occur at a patient location, such as at home, at work, or others, at a pharmacy location, such as at a retail kiosk or others, at a manufacturer location, such as at a warehouse or others, or others. As per block 506, responsive to such reading, the processor 104 switches the medical device 108 from a first mode, such as a deactivated mode, to a second mode, such as an activated mode. In some embodiments, the processor 104 instructs the output device of the system 100A to communicate with the storage medium in order to deactivate the storage medium, as disclosed herein, such as via deleting the content from the storage medium, reformatting the card, or others. As per block 508, the processor 104 tracks usage of the medical device 108 in order to be compliant with the content of the storage medium as read by the input device 110. For example, if the content mandates 1 use during 24 hours for 1 week, then the processor 104 track time, days, and usage per day or another time period (e.g., minutes, hours). As per block 508, if the processor 104 determines that the usage of the medical device has reached a predetermined threshold, as per the content read from the storage medium, then the processor 104 switches the medical device 108 from the second mode (the activated mode) to the first mode (the deactivated mode), otherwise the processor 104 allows the usage of the medical device 108. For example, if the content mandates 1 use during 24 hours for 1 week, then the processor 104 switches the medical device 108 from the second mode to the first mode when 1 week from first use of the medical device 108 passed.

Figure 6B:
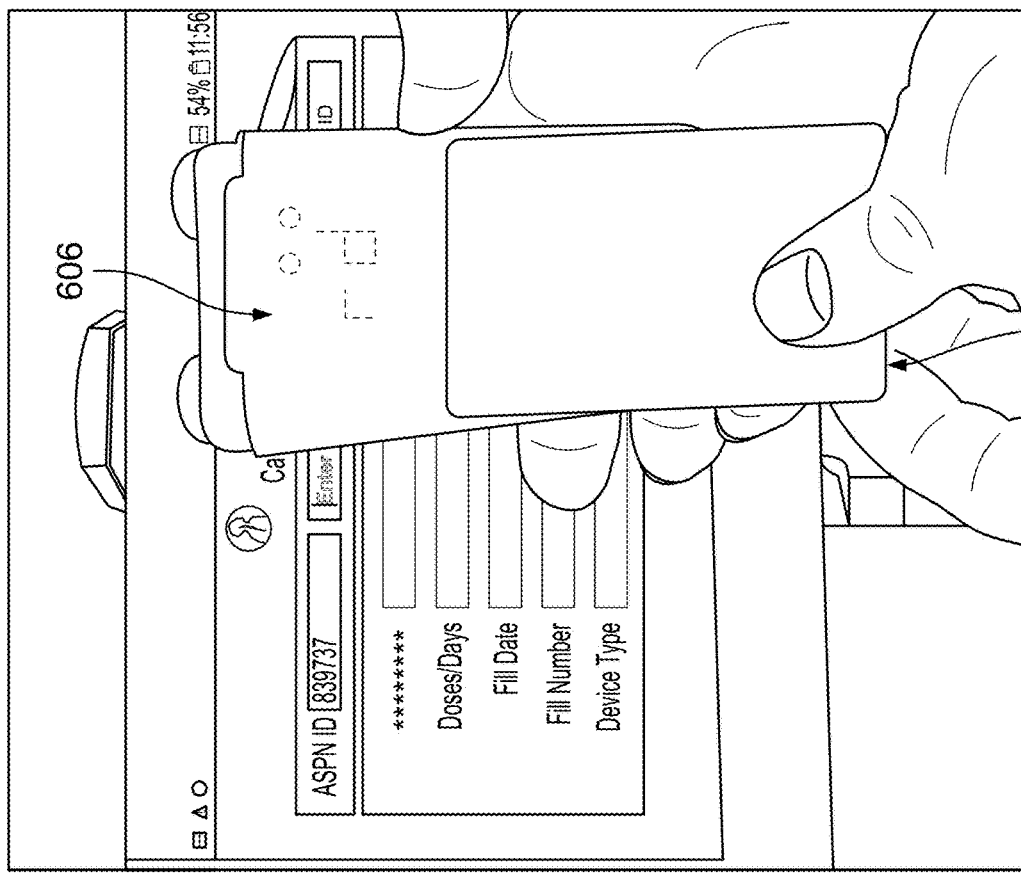
FIGS. 6A, 6B show an embodiment of a technique for pairing a patient/card and a medical device thereby establishing a master patient/card to device mapping according to this disclosure.
Figure 6A:
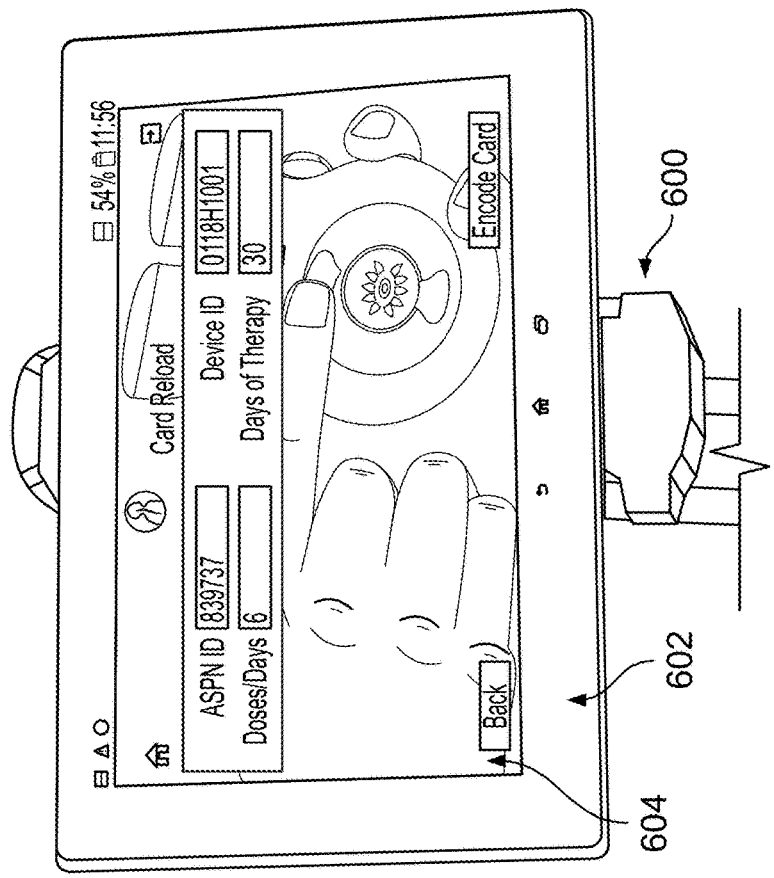
Figure 6C:
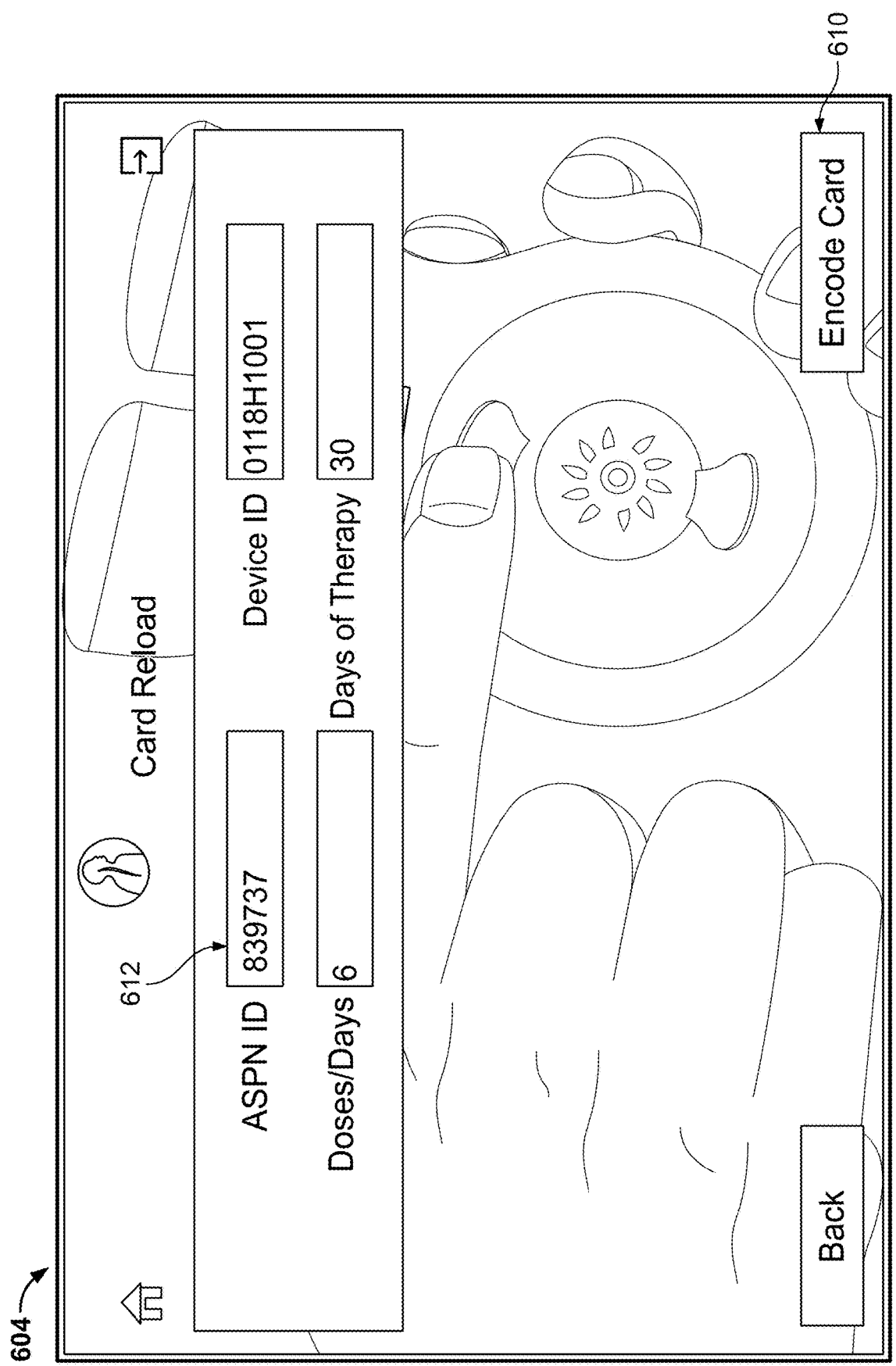
FIG. 6C shows an embodiment of a graphical user interface (GUI) for programming a storage medium according to this disclosure.

FIGS. 6A, 6B show an embodiment of a technique for pairing a patient/card and a medical device thereby establishing a master patient/card to device mapping according to this disclosure. FIG. 6C shows an embodiment of a GUI for programming a storage medium according to this disclosure. As shown in FIG. 6A, a POS terminal 600 includes a touch-enabled display 602 that displays a wizard 604. The POS terminal 600 also includes a camera, whether front or back, and can include a flash illumination device, whether front or back. The POS terminal 600 runs the wizard 604, whether as a local process or over a network connection from a remote data source, such as via browsing or streaming. As shown in FIG. 6B, a neurostimulator 606 is positioned adjacent to a card 608, which may include a physical contact therebetween or be contactless therebetween, such within about 12 inches or less therebetween, although greater distances are possible, such as over a personal area network (PAN), a LAN, or a WAN. As shown in FIG. 6C, the wizard 604 contains a plurality of pages and at least one of the pages presents a plurality of display fields 612 and a plurality input elements 610.

As such, in order to initially provision or refill the neurostimulator 606 for a neurostimulation (or another medical modality) session, as shown in FIGS. 6A and 6C, a user of the POS terminal 600 touch-interacts with the wizard 604 on the display 602 via the input elements 610. In response, the POS terminal 600 communicates with a remote data source, such as over the network 202 with the server 210 of FIG. 2, and receives a set of initial provisioning or refill data from the remote data source for a patient, whether identical to or different from the user. The POS terminal 600 then displays the set of initial provisioning or refill data via the display fields 612. For example, the display fields 612 display a patient identifier, such as an alphanumeric string, a device identifier, such as an alphanumeric string, a dosage amount, such as a numeric string, and a days of therapy amount, such as a numeric string. For example, there can be about 10, 31, or 93 (or less or more) days or uses of therapy as prescribed by a medical service provider, such as a physician. For example, the dosage amount can be about 2 minutes as prescribed by a medical service provider, such as a physician. Resultantly, the user positions the card 608 adjacent to the POS terminal 600 and then further touch-interacts with the wizard 604 such that the POS terminal 600 programs the card 608 in accordance with the set of initial provisioning or refill data, as presented via the display fields 612. Note that the POS terminal 600 can program the card 608 in a wired manner, such as via a card reader of the POS terminal 600, or in a wireless or waveguide manner, such as via a transceiver of the POS terminal 600. Accordingly, as shown in FIG. 6B, the card 608, as pre-programmed via the POS terminal 600, is positioned adjacent (e.g., within about 10 feet or less) to the neurostimulator 606 such that the neurostimulator 606 switches from a first mode, such as a deactivated mode, to a second mode, such as an activated mode, as disclosed herein. In some embodiments, the POS terminal 600 can include a cash register that communicates with a tablet, whether in wired, wireless, or waveguide manner, such that the POS terminal 600 and the tablet are distinct physical devices, with the tablet being used to programmatically initially provision or refill the card 608, which can include via communication with the POS terminal 600. Note that the tablet is illustrative and other computing devices can be used, whether additionally or alternatively, such as smartphone, laptop, desktop, eyewear unit, wearable, or others.

Figure 7:
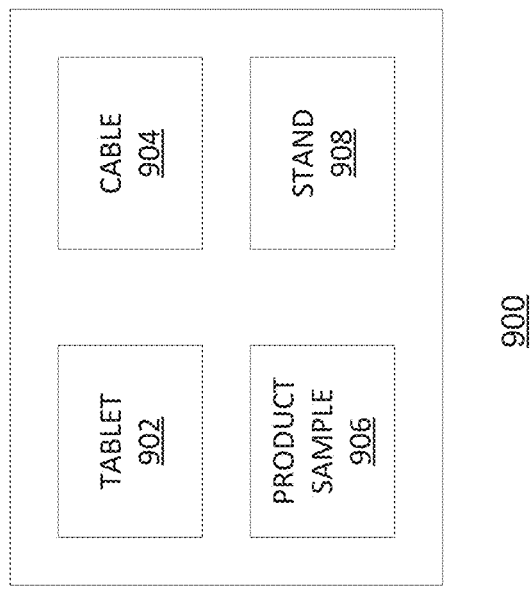
FIG. 7 shows an embodiment of a kit according to this disclosure.

FIG. 7 shows an embodiment of a kit according to this disclosure. A kit 900 includes a tablet 902, a cable 904, a product sample 906, and a stand 908. For example, the tablet 902, the cable 904, the product sample 906, and the stand 908 can be hosted within a package, whether snugly or non-snugly, such as a cardboard box, a plastic pack, a fabric container, an intermodal container, or others. The tablet 902 can be used as a POS terminal, as disclosed herein. The cable 904 can charge the tablet 902 from a wall socket or from a computing device. The cable 904 can also be used for transferring data to or from the tablet 902. For example, the cable 904 can be a USB cable, a Firewire cable, or others. The product sample 906 can include a product label, which can include a barcode, such as a QR code. The stand 908 can support the tablet 902 when the tablet 902 is used as a POS terminal, as disclosed herein. Note that the tablet 902 can also be used without the stand 908.

The tablet 902 hosts a plurality of apps and is configured to operate in a plurality of modes, including a pharmacy admin mode and a pharmacy agent mode. The apps include initial provisioning and refilling (IPAR) app, which can interface with a remote or local data source when running on the tablet 902, whether the tablet 902 is in wired, wireless, or waveguide communication with the remote data source. The tablet 902 can receive the IPAR app from a network-based data source, such as a server (e.g., physical, virtual, web, application, database), or from a memory load, such as via a memory stick, or others. The tablet 902 controls access to the modes based on a user login, which may be via passwords, two factor authentication, biometrics (e.g., fingerprints, retina scans), or others. In some embodiments, the tablet 902 controls access to the modes based on the user login into the IPAR app. The pharmacy admin mode grants an administrator level access to functionality of the tablet 902 and the apps hosted thereon, including the IPAR app. The pharmacy agent mode grants a limited user level access to functionality of the tablet 902 such that the tablet 902 is operated in a kiosk mode involving the IPAR app. For example, in the pharmacy agent mode, a user may be prevented from accessing any, some, most, or all apps other than the IPAR app. Note that the modes may display various visually distinct indicia notifying of what mode the tablet 902 is operating in. For example, the visual indicia can include icons, alphanumeric labels, graphics, images, watermarks, backgrounds, fonts, or any other visual elements, where the visual indicia differ between the modes.

Figure 8A:
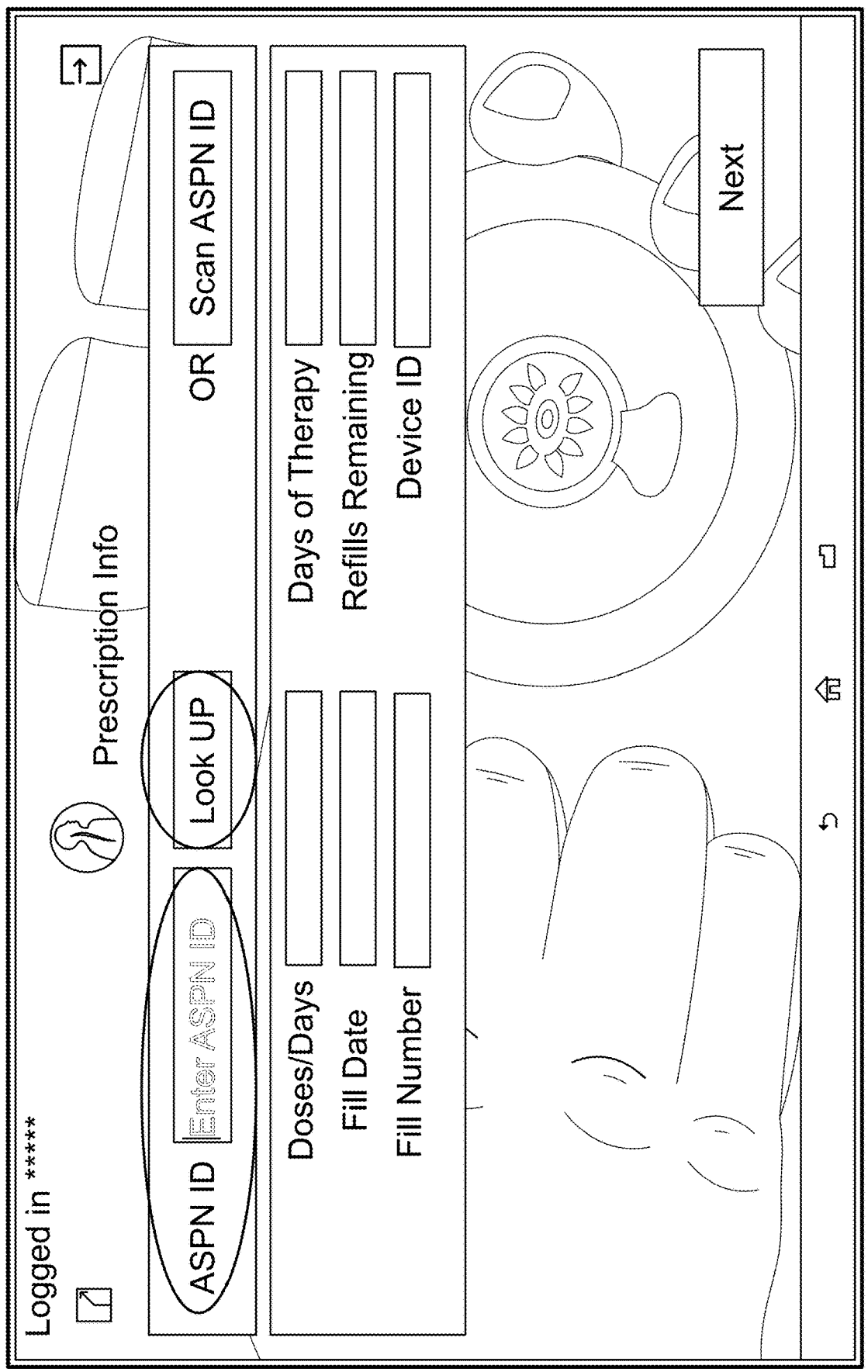

FIGS. 8A-8G show an embodiment of a process of pairing a patient/card and a medical device thereby establishing a master patient/card to device mapping according to this disclosure. The wizard 604 is used in this process and, as shown in FIG. 8A, the user operates the POS terminal 600 to input a referral identifier, such as an alphanumeric string, into one of the display fields 612 and interacts with one of the input elements 610 to submit the referral identifier to the remote data source for retrieving the set of initial provisioning or refill data.

Figure 8B:
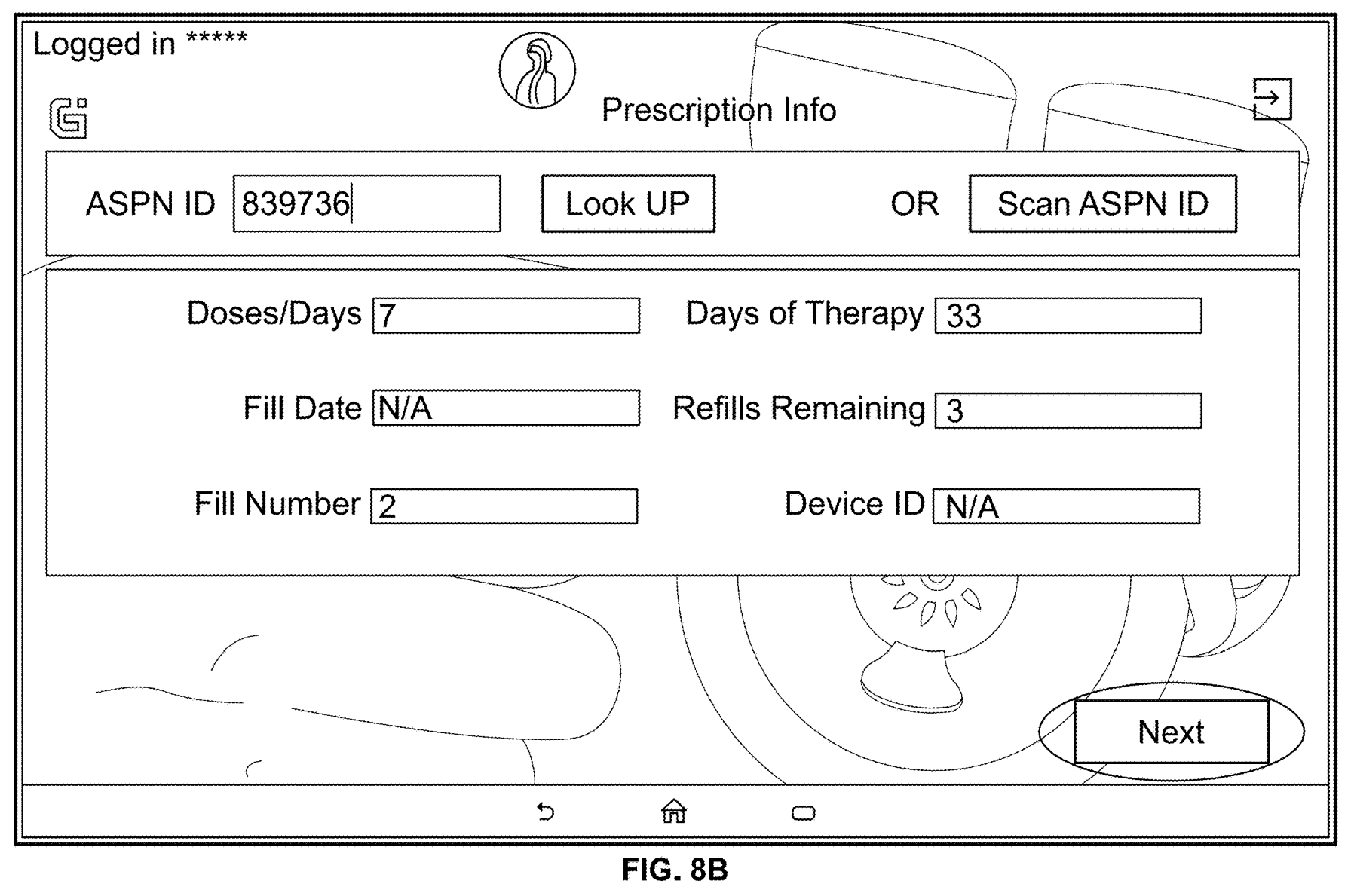
Figure 8C:
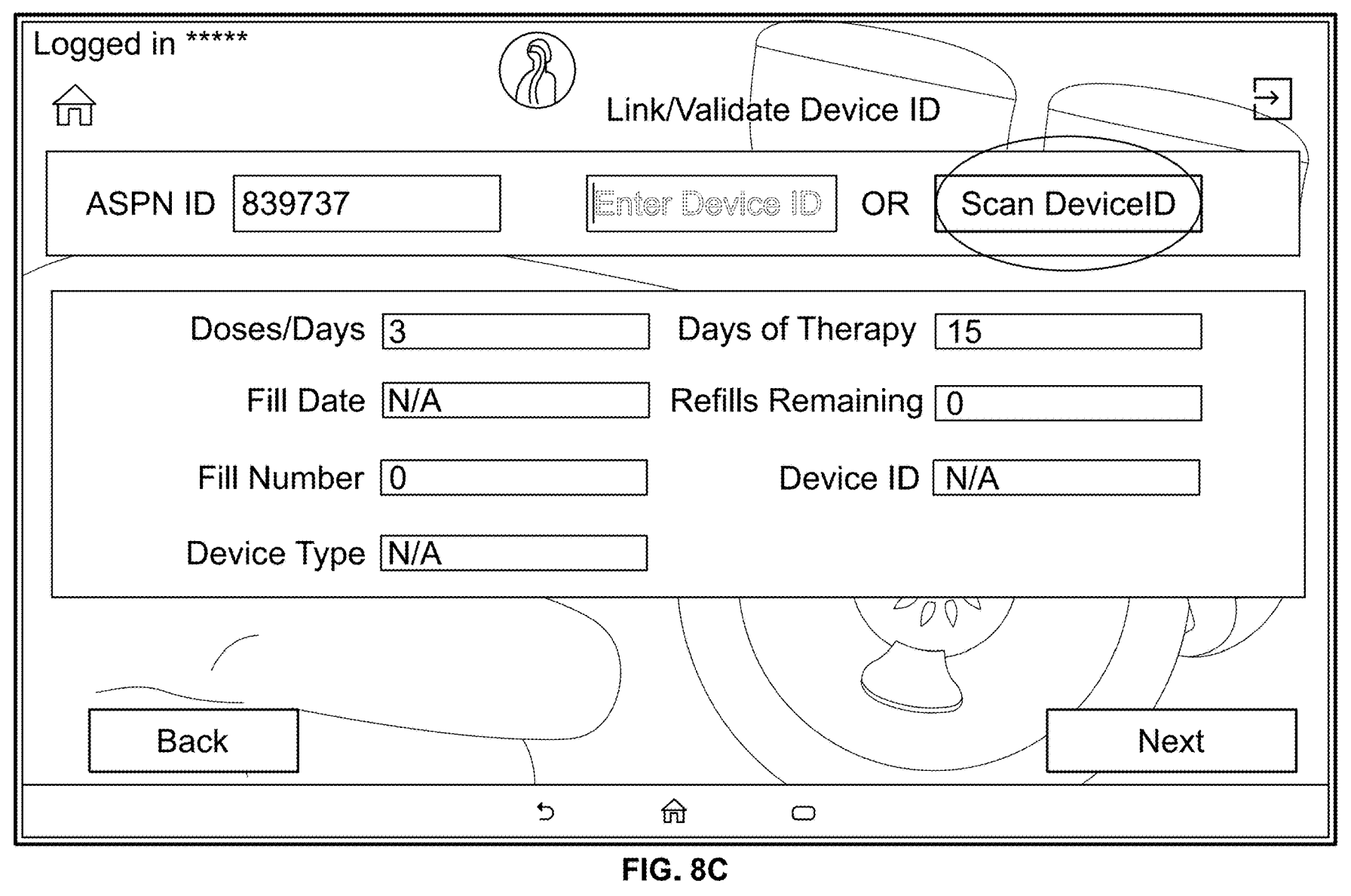

As shown in FIG. 8B, the remote source retrieves the set of initial provisioning or refill data and sends the set of initial provisioning or refill data to the POS terminal 600 such that the POS terminal 600 populates some, most, or all remaining display fields 612 with corresponding information extracted or copied from the set of initial provisioning or refill data. Note that if such remaining display fields 612 do not populate or do not fully populate, then such error may be due to the referral identifier being incorrectly entered or being invalid. Further, note that upon such lack of population or lack of full population, the POS terminal 600 may display a warning message via the wizard 604, with the warning message requesting re-entry of the referral identifier or suggesting a call to a predetermined phone number, which may be remotely updatable.

As shown in FIG. 8C, the user again operates the POS terminal 600 to have the POS terminal 600 optically read the neurostimulator 606 (or another medical device) via the camera, such as via barcode scanning.

As shown in FIG. 8D, the user selects the neurostimulator 606 from an inventory and holds the neurostimulator device 606 with a label having a barcode facing up behind POS terminal 600 such that the camera of the POS terminal 600 can read the barcode. Note that the neurostimulator 606 can be packaged within a package, such as a cardboard box or others, as explained herein, where the package or the neurostimulator 606 hosting the label, or be outside of the package, with the package or the neurostimulator 606 hosting the label. As such, the POS terminal 600 captures an image of the barcode.

As shown in FIG. 8E, as the POS terminal 600 focuses on capturing the barcode, the POS terminal 600 displays a bounding box (e.g., square, rectangle, oval, circle, triangle, pentagon, octagon, hexagon, polygon) or another closed shape (e.g., O-shape, D-shape) or open shape (e.g., U-shape, C-shape) extending around or about the barcode within the display 602. Further, note the POS terminal 600 can display multiple bounding boxes, which are visually distinct from each other, such as via color, shape, background, foreground, line style, or others. Moreover, note that the barcode is scanned by aligning the bounding box over the barcode such that the barcode is positioned within the bounding box and activating, such as via touching the display 602, the bounding box to capture the image of the barcode. Additionally, note that in poor illumination conditions, the POS terminal 600 can activate the flash illumination device to assist in capturing the image of the barcode. Furthermore, if the POS terminal 600 is unable to capture the barcode, then the wizard 604 presented on the POS terminal 600 enables a manual entry of a device identifier, which may be validated against a set of device identifiers, whether stored locally on the POS terminal 600 or stored or accessible via the remote data source.

Figure 8F:
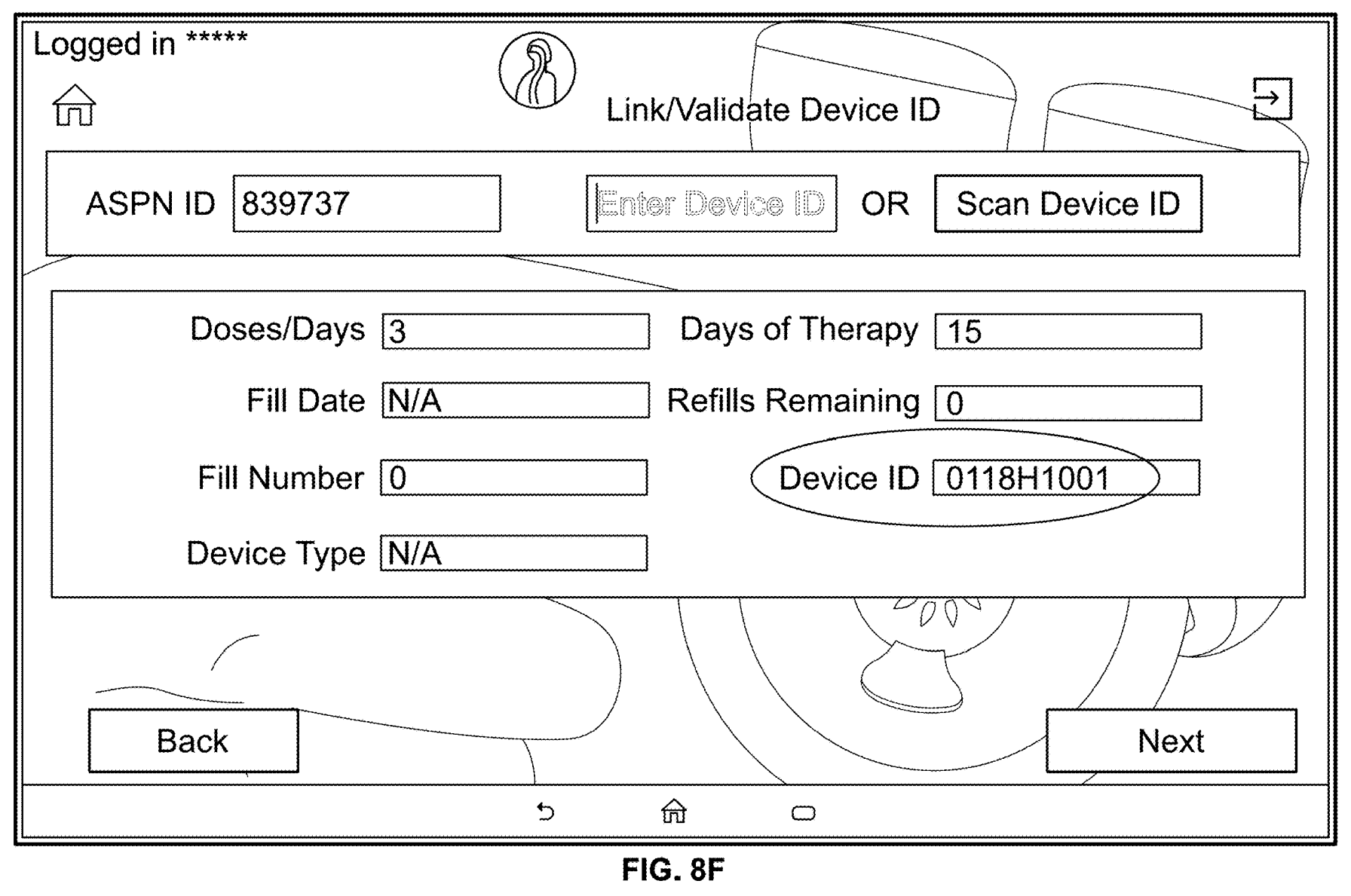

As shown in FIG. 8F, after the POS terminal 600 captures the image that depicts the barcode, the POS terminal 600 processes the image to extract, which may include format or value conversion, a device identifier, such as an alphanumeric string, from the image, such as via various optical character recognition and other computer vision techniques, and populates the device identifier into one of the display fields 612.

Figure 8G:
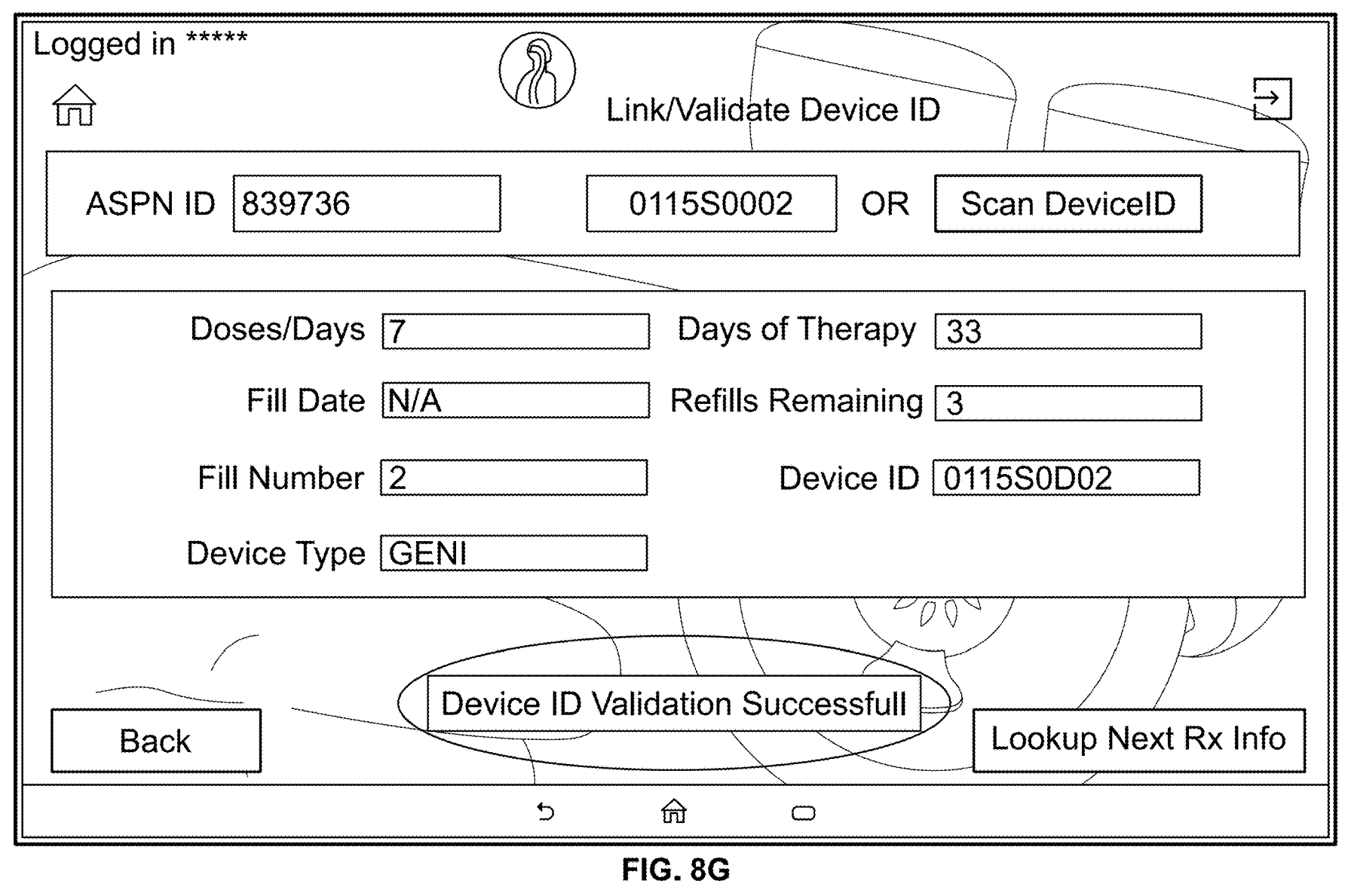

As shown in FIG. 8G, the POS terminal 600 displays a message when the device identifier is successfully validated and mapped, in a one-to-one correspondence, to the referral identifier, e.g. the NPI number or ASPN ID associated with a prescription. As such, the user of the POS terminal 600 can iteratively proceed with mapping another referral identifier with another device identifier. In this manner, a prescription from a healthcare provider (e.g., doctor, therapist) may be associated with a specific device by linking, in one to one correspondence, a patient card to a device identifier. For example, the one-to-one correspondence can mean that the patient card, whether an initial card or a refill, will only be recognized by and usable to activate/refill the specific device which bears the unique device identifier associated with the patient card at the time the patient card was filled or authorized. In a case of an initial satisfaction of a prescription, in which a patient receives a device for a first time, the unique identifier of the device is retrieved and matched with a prescription and patient card by scanning the device (e.g., by scanning a barcode or interrogating an RFID chip associated with the device), scanning the patient card (e.g. by scanning a barcode or interrogating an RFID chip associated with the patient card), and activating the patient card to contain prescription information, such as doses or a designated time period of use or others. Thereafter, when the patient card is held up to the device, the device identifier programmed into the patient card will be recognized by the device and/or card, and the prescription information will be transferred (e.g., wired, wirelessly, waveguide) to the device. If the device identifier programmed into the patient card does not match the device identifier of the device, then at least some, most, or all prescription authorization information will not be transferred to the device. When a patient requires a prescription refill, then a new prescription is obtained (e.g., electronically) from the healthcare provider and submitted (e.g., electronically) to the pharmacy. The pharmacy will program (e.g., keying) the patient card with prescription information, and with the unique patient device identifier associated with the patient's device. The patient's device need not be present during the refill process because a system database contains the device identifier associated with the device previously issued to the patient, so the pharmacy can program the patient card with the appropriate dosage information contained in the prescription, and associate the patient card to be uniquely associated with the device identifier of the patient's device, and only that device. Such a system has a technical advantage or benefit of assuring that the prescribed treatment information may only be transferred from the patient card to the device possessed and previously assigned to the intended patient, and not any other patient or device.

Note that all aspects, characteristics, or components of initial provisioning or refilling of a medical device, as described herein, or all uses (e.g., prevention, diagnosis, monitoring, amelioration, or therapy related mechanical, thermal, acoustic, optical, vibratory, digital, data, or electronic acts) of the medical device, as described herein, or all uses of a storage medium (e.g., access, read, write, modify, copy, delete, format, encrypt, decrypt, load, unload, send, receive) can be written or uploaded to a block of a blockchain local to or remote from the medical device or the storage medium. For example, the system 100A can include or communicate with a node of a blockchain of a blockchain network. The node can enable writing, reading, modifying, copying, or deleting operations relative to a block of the blockchain. These operations can track initial provisioning, refilling, or all usages of the medical device or the storage medium for at least medical device or storage medium recordkeeping purposes (e.g., EMR, prescription, billing, device maintenance, device updates, system security).

Figure 9A:
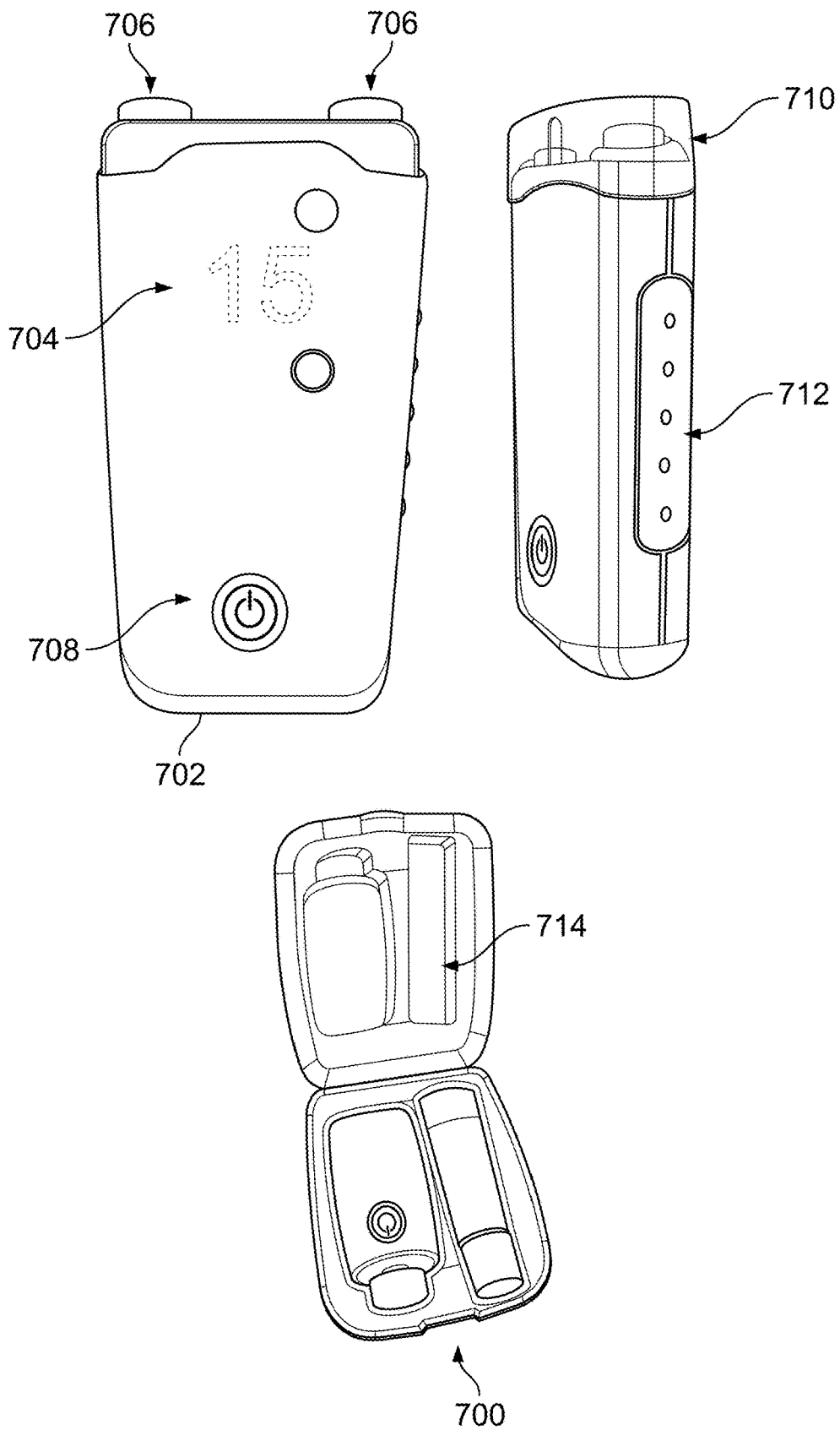
Figure 9E:
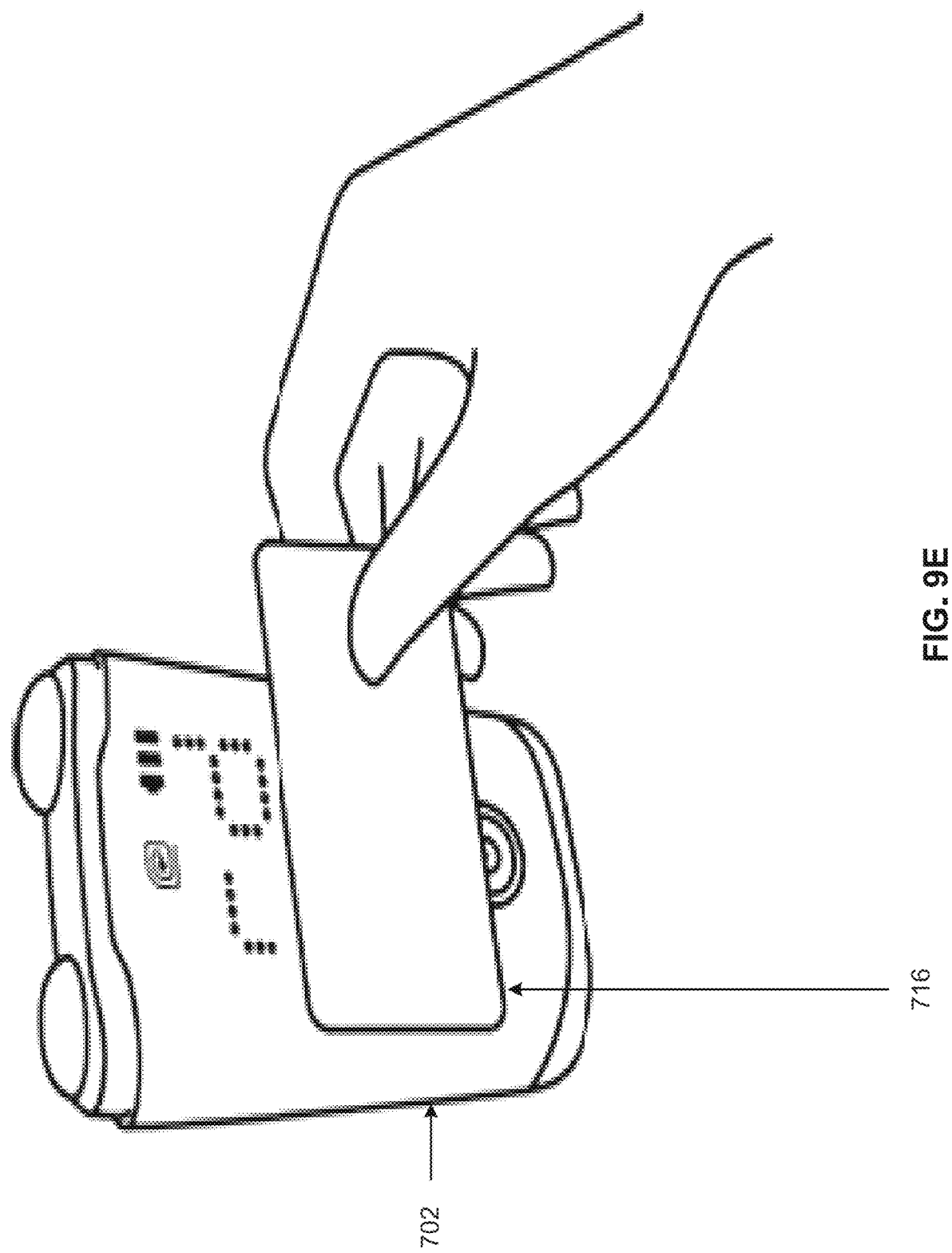
Figure 9F:
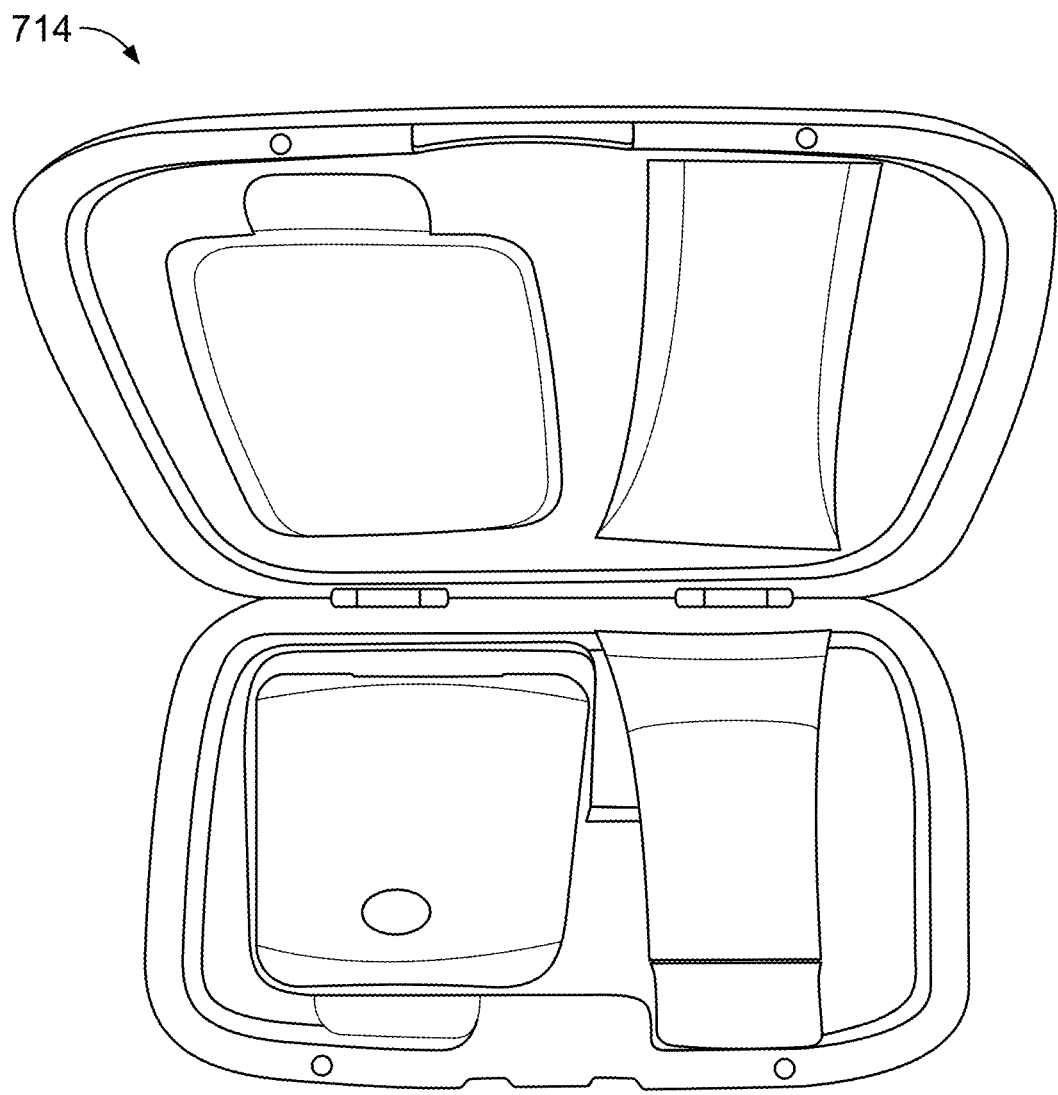
Figure 9G:
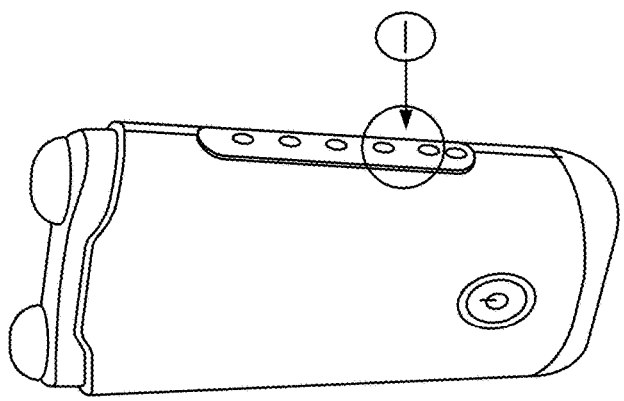

FIGS. 9A-9J show an embodiment of a neurostimulator according to this disclosure. As shown in FIGS. 9A and 9G, a neurostimulator 700 can be used to provide non-invasive stimulation of a nerve. For example, the stimulation may be via an electrical energy, a mechanical energy, a thermal energy, an acoustic energy, a vibratory energy, or others. For example, the stimulation may be at a side of a neck of a patient. For example, the nerve can be a vagus nerve, a cranial nerve, a trigeminal nerve, a spinal nerve, or others.

The neurostimulator 700 includes a housing 702, a display 704, a plurality of stimulation surfaces 706, a power button 708, a cap 712, and a control button 714. In some embodiments, the neurostimulator 700 includes a speaker housed via the housing 702 and powered via the battery. In some embodiments, the neurostimulator 700 includes a microphone housed via the housing 702 and powered via the battery. The housing 702 houses a signal generator and a battery. The housing 702 is opaque, but can be transparent. The battery powers the signal generator and the display. The power button 708 turns the neurostimulator 700 on and off. The button 708 can be a mechanical button or a touch-enabled surface, which can be haptic or configured to receive a touch input, a slide input, a gesture input, or others. The stimulation surfaces 706 contact a skin of a patient and conduct a stimulation energy, such as an electrical current, an electrical impulse, an actuation, or others, from the signal generator to the skin of the patient.

The display 704, which can present in monochrome, grayscale, or color, indicates a status of the neurostimulator 700, such as on, off, charging, dosage amount total, dosage amount remaining, stimulation time total, stimulation time remaining, or others. The display 704 can be of any type, such as a segment display, a liquid crystal display (LCD), an electrophoretic display, a field emission display (FED), or others, whether rigid, elastic, resilient, bendable, or flexible. The display 704 can be configured to receive a touch-input, including a gesture, a slide, or others. The cap 712 is mounted to the housing 702, such as via snug fit, friction, fastening, mating, adhering, or others. The cap 712 is transparent, but can be opaque. The cap 712 covers and protects the stimulation surfaces 706 from mechanical damage, interference, moisture, or others. The control button 714 is operably coupled to the signal generator and is thereby configured to increase or decrease an intensity of the stimulation by controlling the signal generator. The control button 714 can be a mechanical button or a touch-enabled surface, which can be haptic or configured to receive a touch input, a slide input, a gesture input, or others. The neurostimulator 700 can be charged via a charging station 716, whether in a wired, wireless, or waveguide manner.

For example, the neurostimulator 700 can be a multi-use, hand-held, rechargeable, portable device comprising of a rechargeable battery, a set of signal-generating and amplifying electronics, and a control button for operator control of a signal amplitude. The device provides visible (display) and audible (beep) feedback on the device and stimulation status. A pair of stainless steel surfaces, which are a set of skin contact surfaces, allows a delivery of an electrical signal. The patient applies an electrode gel to the contact surfaces to maintain an uninterrupted conductive path from the contact surfaces to the skin on the neck of the patient. The stimulation surfaces are capped when not in use. The neurostimulator 700 can produce a low voltage electric signal including about five 5,000 Hz electric pulses (or less or more) that are repeated at a rate of 25 Hz (or less or more). A waveform of the electric pulses is approximately a sine wave with a peak voltage limited to about 24 volts (or less or more) when placed on the skin of the neck of the patient and a maximum output current of 60 mA (or less or more). The signal is transmitted through the skin of the neck to the vagus nerve. The neurostimulator 700 allows the patient to appropriately position and adjust a stimulation intensity as instructed a healthcare provider. Further details of appropriate waveforms and electrical signals and how to generate and transmit such signals to a desired nerve can be found in U.S. Pat. Nos. 8,874,205; 9,333,347; 9,174,066; 8,914,122 and 9,566,426, which are incorporated herein in their entireties by reference for at least these purposes as if copied and pasted herein, as disclosed herein, and for all purposes as if copied and pasted herein, such as all structures, all functions, and all methods of manufacture and use, as disclosed therein. Each dose can be applied for two minutes, after which the neurostimulator automatically stops delivering the neurostimulation. The neurostimulator 700 can allow for single or multiple uses or sessions. The neurostimulator can deliver a fixed number of treatments within a 24-hour period (or less or more). Once a maximum daily number of treatments has been reached, the neurostimulator 700 will not deliver any more treatments until a following 24-hour period expires. The neurostimulator can be charged via a charging station. The neurostimulator can allow for a fixed number of treatments within a defined time period, such as thirty one days or ninety three days, or some other period of time.

The display 704 is able to present a plurality of symbols that are informative of various states of the neurostimulator 700. As such, FIGS. 9B-9D show a table of symbols that can be displayed via the display 704 as icons and a set of corresponding explanations of the symbols. In embodiments where the neurostimulator 704 includes the speaker, the table explains various sounds that can be output via the speaker. Note that such symbols and sounds are illustrative and can vary in color, shape, frequency, geometrical perimeter/volume, acoustical parameters, or others.

As shown in FIG. 9E, the neurostimulator 700 can be switched between a first mode and a second mode based on a card 716 being positioned in proximity thereof, whether via contact or avoiding contact, whether blocking the display 704 or below the display 704, as explained above. Note that the display 704 displays (1) a symbol informative of the card 716 being read via the neurostimulator 700, (2) a symbol informative of the battery of the neurostimulator 700 being full, and (3) a symbol informative of the neurostimulator 700 being reloaded via the card 716, as explained above. Also, note that the neurostimulator 700 can read the card 716 when the neurostimulator 700 is turned on. Further, note that if the neurostimulator 700 includes the speaker, then the neurostimulator 700 can output the sound alternative or additional to the display 704 displaying an appropriate symbol.

As shown in FIG. 9F, the charging station 716 can be used to recharge the neurostimulator 700. The charging station 716 includes a power adapter. As such, the power adapter can be plugged into a power outlet and with the power button 708 facing up, the housing 702 can be placed into the charging station 716, with the housing 702 snugly fitting into the charging station 716. Next, the display 704 can display a symbol informative of the battery of neurostimulator 700 being charged. For example, such symbol can change dynamically, such as via flashing, growing/increasing in perimeter/volume, or others. When the battery is fully charged, then the display 704 can display a symbol informative of such status. Note that if the battery is not being charged within the charging station 716, then the display 704 can display a symbol informative of such status or a symbol informative of an error status.

Figure 9H:
Figure 9H:
Figure 9H:
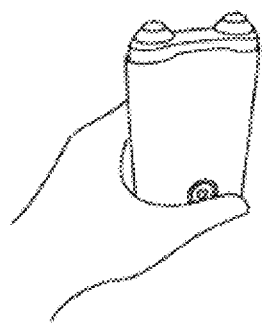
Figure 9I:
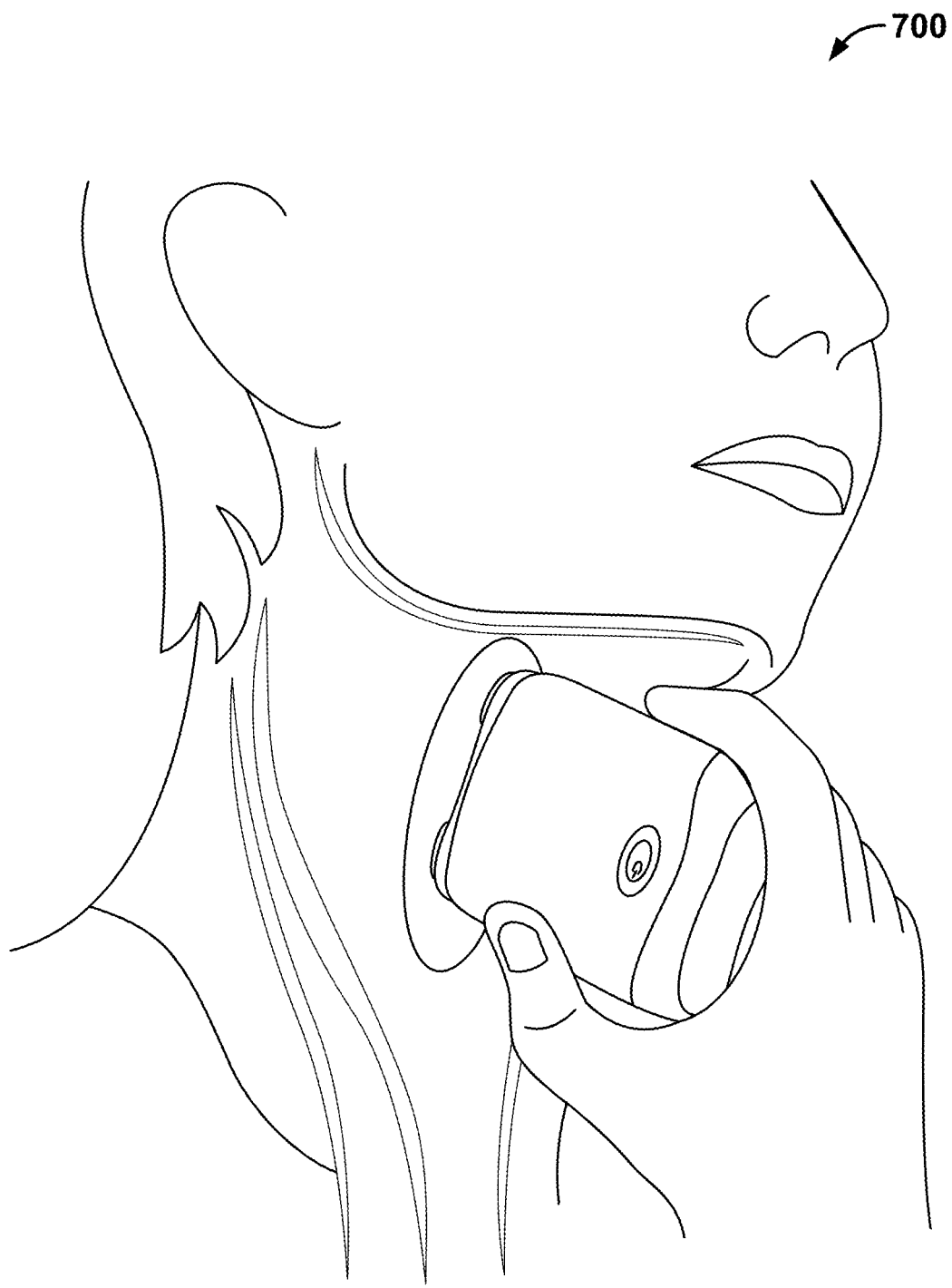

As shown in FIGS. 9H and 9I, the neurostimulator 700 can be used by removing the cap 712 from the housing 702, applying an energy conductive gel to the stimulation surfaces 706, and the positioning the stimulation surfaces 706 adjacent to the skin of the patient. In some embodiments, the energy conductive gel can be applied to the skin of the patient. Then, the power button 708 is turned on and the display 704 can display one or more symbols suitable at that time, as explained above. In embodiments where the housing 702 houses the speaker, then the speaker can output one or more sounds suitable at that time, as explained above. Note that the user can increase the intensity of stimulation by repeatedly pressing a top area of the control button 714 to a maximum level the user can tolerate. In embodiments where the neurostimulator 700 includes the speaker, the neurostimulator 700 can output a sound every time the control button 714 is pushed and the display 704 can indicate a numerical value between 1 and 40, although other information systems are possible, such as iconic or alphabetic, which signifies a level of stimulation.

Figure 9J:

As shown in FIG. 9J, after the patient completes a session of neurostimulation, the display 704 will display a number of doses and days remaining and a last stimulation level before automatically turning off. In embodiments where the neurostimulator 700 includes the speaker, the neurostimulator 700 can stop automatically after two minutes (or less or more) and the speaker can output a sound informative of such action and automatically stop stimulation. Note that a number of days and doses remaining can be viewed by turning the neurostimulator 700 on. Similarly, the stimulation surfaces 706 can be cleaned by wiping any leftover gel off the stimulation surfaces 706 with a soft dry cloth. Moreover, the cap 712 can be placed back onto the housing 702.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

Various diagrams depicted herein are illustrative. There can be many variations to such diagrams or steps (or operations) described therein without departing from various spirits of this disclosure. For instance, various steps can be performed in a differing order or steps can be added, deleted or modified. All of these variations are considered a part of this disclosure. People skilled in an art to which this disclosure relates, both now and in future, can make various improvements and enhancements which fall within various scopes of various claims which follow.

This detailed description has been presented for various purposes of illustration and description, but is not intended to be fully exhaustive and/or limited to this disclosure in various forms disclosed. Many modifications and variations in techniques and structures will be apparent to those of ordinary skill in an art without departing from a scope and spirit of this disclosure as set forth in various claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. A medical device comprising:
   a housing;
   a power supply coupled to the housing;
   a signal generator and one or more electrodes coupled to the housing, wherein the signal generator is configured to apply one or more electrical impulses to the one or more electrodes for a period of time, the period of time being defined as a single dose; and
   a software application configured for coupling to the power supply, wherein the software application switches the device from an activated mode to a deactivated mode after a specific number of single doses have been emitted by the signal generator.

2. The device of claim 1, wherein the specific number of single doses is about 1000 or less.

3. The device of claim 1, wherein the specific number of single doses is about 100 or less.

4. The device of claim 1, wherein the single dose has a time period of about thirty seconds to about 5 minutes.

5. The device of claim 1, wherein the single dose has a time period of about ninety seconds to about 3 minutes.

6. The device of claim 1, wherein the medical device is a neurostimulator, wherein the signal generator transmits the one or more electrical impulses from the one or more electrodes through the contact surface transcutaneously and non-invasively through an outer skin surface of a patient such that the one or more electrical impulses modulates a nerve within the patient.

7. The device of claim 6, wherein the one or more electrical impulses modulates a vagus nerve and causes the vagus nerve to generate an action potential to treat a medical condition within the patient.

8. The device of claim 1, wherein the signal generator and the power supply are housed within the housing.

9. A method comprising:
   controlling a software application to cause a medical device to be switched from a deactivated mode to an activated mode;
   applying one or more electrical impulses to one or more electrodes with the medical device for a period of time, the period of time being defined as a single dose;
   controlling the software application to track a number of single doses applied by the medical device; and
   controlling the software application to cause the medical device to be switched from the activated mode to the deactivated mode after a specific number of single doses have been applied by the medical device.

10. The method of claim 9, wherein the specific number of single doses is about 1000 or less.

11. The method of claim 9, wherein the specific number of single doses is about 100 or less.

12. The method of claim 9, wherein the single dose has a time period of about thirty seconds to about 5 minutes.

13. The method of claim 9, wherein the single dose has a time period of about ninety seconds to about 3 minutes.

14. The method of claim 9, further comprising transmitting the one or more electrical impulses from the one or more electrodes through the contact surface transcutaneously and non-invasively through an outer skin surface of a patient such that the one or more electrical impulses modulates a nerve within the patient.

15. The method of claim 9, wherein the one or more electrical impulses are sufficient to modulate a vagus nerve and causes the vagus nerve to generate an action potential to treat a medical condition within the patient.

* * * * *